US011779677B2

(12) United States Patent
Chen et al.

(10) Patent No.: US 11,779,677 B2
(45) Date of Patent: Oct. 10, 2023

(54) PHOTOCATALYTIC OXIDATION CENTRIFUGAL FAN

(71) Applicants: TRANE AIR CONDITIONING SYSTEMS (CHINA) CO., LTD., Jiangsu (CN); TRANE INTERNATIONAL INC., Davidson, NC (US)

(72) Inventors: Xuefeng Chen, Taicang (CN); Bang Yu Wang, Taicang (CN); Qing Hao Wang, Taicang (CN); De Bin Cao, Taicang (CN)

(73) Assignees: TRANE AIR CONDITIONING SYSTEMS (CHINA) CO., LTD., Taicang (CN); TRANE INTERNATIONAL INC., Davidson, NC (US)

( * ) Notice: Subject to any disclaimer, the term of this patent is extended or adjusted under 35 U.S.C. 154(b) by 274 days.

(21) Appl. No.: 17/090,626

(22) Filed: Nov. 5, 2020

(65) Prior Publication Data

US 2022/0096703 A1 Mar. 31, 2022

(30) Foreign Application Priority Data

Sep. 27, 2020 (CN) ......................... 202011033778.4
Sep. 27, 2020 (CN) ......................... 202022157496.7

(51) Int. Cl.
*A61L 9/20* (2006.01)
*F04D 29/42* (2006.01)
(Continued)

(52) U.S. Cl.
CPC ............ *A61L 9/205* (2013.01); *F04D 29/281* (2013.01); *F04D 29/4226* (2013.01);
(Continued)

(58) Field of Classification Search
CPC ..... A61L 9/205; F24F 3/16; F24F 8/22; F24F 1/0022; F04D 29/281; F04D 29/283; F04D 29/4226
See application file for complete search history.

(56) References Cited

U.S. PATENT DOCUMENTS 1,862,523 A 6/1932 Anderson
2,727,680 A 12/1955 Madison et al.
(Continued)

FOREIGN PATENT DOCUMENTS

CN 202659576 * 1/2013
CN 204438264 * 7/2015
(Continued)

*Primary Examiner* — Brian O Peters
(74) *Attorney, Agent, or Firm* — Hamre, Schumann, Mueller & Larson, P.C.

(57) ABSTRACT

A centrifugal fan for a heating, ventilation, air conditioning, and refrigeration (HVACR) system is disclosed. The centrifugal fan includes a volute housing having an inner surface and a curved inlet shroud. The volute housing defines an air outlet. The curved inlet shroud defines an air inlet. The air inlet has an inlet airflow cross-sectional area that lies substantially perpendicular to an outlet airflow cross-sectional area of the air outlet. The centrifugal fan also includes an impeller mounted for rotation about a rotational axis within the volute housing. The impeller has a plurality of fan blades. The plurality of fan blades has an outer surface. The centrifugal fan further includes a light source. The inner surface of the volute housing and the outer surface of the plurality of fan blades includes a photocatalyst layer. The light source is configured to emit light on the photocatalyst layer.

19 Claims, 20 Drawing Sheets

(51) Int. Cl.

| | |
|---|---|
| ***F04D 29/28*** | (2006.01) |
| ***F04D 29/70*** | (2006.01) |
| ***F24F 1/0022*** | (2019.01) |
| ***F24F 8/22*** | (2021.01) |

(52) U.S. Cl.

CPC .......... *F04D 29/701* (2013.01); *F24F 1/0022* (2013.01); *A61L 2209/12* (2013.01); *A61L 2209/16* (2013.01); *F24F 8/22* (2021.01)

(56) References Cited

U.S. PATENT DOCUMENTS

| | | | | | |
|---|---|---|---|---|---|
| 2,798,658 | A | | 7/1957 | McDonald | |
| 2,951,630 | A | | 9/1960 | Murphy | |
| 2,981,461 | A | | 4/1961 | Murphy | |
| 3,008,305 | A | * | 11/1961 | Reiss | F24F 1/031 62/427 |
| 3,217,976 | A | | 11/1965 | Downs | |
| 3,221,983 | A | | 12/1965 | Trickler et al. | |
| 3,307,776 | A | | 3/1967 | White | |
| 3,627,440 | A | | 12/1971 | Wood | |
| 4,017,652 | A | * | 4/1977 | Gruber | C09D 163/10 427/520 |
| 5,474,422 | A | * | 12/1995 | Sullivan | F04D 29/626 415/206 |
| 5,558,499 | A | | 9/1996 | Kobayashi | |
| 5,570,996 | A | | 11/1996 | Smiley, III | |
| 7,108,478 | B2 | | 9/2006 | Hancock | |
| 7,186,080 | B2 | | 3/2007 | Smiley, III et al. | |
| 7,591,633 | B2 | | 9/2009 | Hancock | |
| 10,428,500 | B2 | * | 10/2019 | Schluttig | E03C 1/28 |
| 2017/0234323 | A1 | * | 8/2017 | Pirouzpanah | F04D 29/424 417/321 |

FOREIGN PATENT DOCUMENTS

| | | | | |
|---|---|---|---|---|
| CN | 106391025 | | * | 2/2017 |
| CN | 207125525 | | * | 3/2018 |
| CN | 108786284 | A | | 11/2018 |
| GB | 2536976 | | * | 5/2010 |
| JP | 4103262 | B2 | * | 6/2008 |

* cited by examiner

900

| Fancoil-2 fans | Baseline | 1 lamp/fan | 2 lamps/fan |
|---|---|---|---|
| Noise dB (A) | 33.4 | 34.6 | 34.7 |
| Change dB (A) | 0 | +1.2 | +1.3 |
| Input power W | 49.4 | 48.6 | 48.1 |
| Airflow CMH@12Pa | 625 | 604 | 575 |
| Change | 0% | -3% | -8% |

PHOTOCATALYTIC OXIDATION CENTRIFUGAL FAN

FIELD

This disclosure relates generally to centrifugal fan(s)/blower(s) for a heating, ventilation, air conditioning, and refrigeration (HVACR) system. More specifically, the disclosure relates to systems and method for configuring and controlling centrifugal fan(s)/blower(s) with photocatalytic oxidation and/or ultraviolet germicidal irradiation technology to improve the efficiency and efficacy of one-time filtration and/or sterilization of air for an HVACR system.

BACKGROUND

Centrifugal fans (or blowers) are widely used for circulating air in residential and commercial HVACR systems. Electric motor driven centrifugal fans having volute housing or scroll type fan housing are particularly widely used in HVACR systems wherein the fan housing is mounted in a cabinet which may also contain heat transfer equipment such as a refrigerant fluid heat exchanger or a furnace heat exchanger, etc.

Currently the world is experiencing a global pandemic. Building owners and operators (commercial, industrial, and residential) have different challenges to address the pathogen (bacteria, fungi, protozoa, worms, viruses, and/or infectious proteins such as prions, etc.) spread, such as more complicated building and space design, an increased populous and densities of people, increased movement of people worldwide and the general increasing interconnectedness of people worldwide, and technologies associated with accommodating these complications and increases. Building owners and operators turn to building policies, procedures, and operations, and also use technology to reduce/kill pathogens and to keep air clean. Further solutions in overcoming such challenges could benefit public health and safety.

SUMMARY

Building owners and operators (commercial, industrial, and residential) have the ability to control conditioned air movement, temperature, humidity and air cleaning technologies within their building. The issue with today's pandemic is that the science around what are best practices to minimize the amount of infection that may occur within the occupied space is still unknown and being studied. Some studies reveal that there may be specific portions of the populace that have proclivity towards higher infection rates and/or higher susceptibility to illness, for example to illness severity of COVID-19.

This disclosure relates generally to centrifugal fan(s)/blower(s) for an HVACR system. More specifically, the disclosure relates to systems and method for configuring and controlling centrifugal fan(s)/blower(s) with photocatalytic oxidation and/or ultraviolet germicidal irradiation technology to improve the efficiency and efficacy of one-time filtration and/or sterilization of air for an HVACR system. It will be appreciated that the HVACR system can be used for building (e.g., residential and/or commercial) spaces as well as for climate controlled transport unit(s) (e.g., transport refrigeration unit(s), and/or tractor cabin, etc.). In an embodiment, the HVACR system can be a climate control unit (CCU).

Embodiments disclosed herein can be used for example to control conditioned air spaces and lighting to reduce or kill pathogens or microbiologicals, reduce susceptibility of occupants to microbiological infection, reduce impact of illness from microbiologicals, and/or reduce pathogen or microbiologicals spread. Embodiments disclosed herein can provide improved health with the presence of microbiological organisms, particulate matter and other airborne substances that may be detrimental to human (or other animal or plant) health.

A centrifugal fan for an HVACR system is disclosed. The centrifugal fan includes a volute housing having an inner surface and a curved inlet shroud. The volute housing defines an air outlet. The curved inlet shroud defines an air inlet. The air inlet has an inlet airflow cross-sectional area that lies substantially perpendicular to an outlet airflow cross-sectional area of the air outlet. The centrifugal fan also includes an impeller mounted for rotation about a rotational axis within the volute housing. The impeller has a plurality of fan blades. The plurality of fan blades has an outer surface. The centrifugal fan further includes a light source. The inner surface of the volute housing and the outer surface of the plurality of fan blades includes a photocatalyst layer. The light source is configured to emit light on the photocatalyst layer A method of configuring a centrifugal fan for an HVACR system is disclosed. The centrifugal fan includes a volute housing having an inner surface and a curved inlet shroud. The volute housing defines an air outlet. The curved inlet shroud defines an air inlet. The air inlet has an inlet airflow cross-sectional area that lies substantially perpendicular to an outlet airflow cross-sectional area of the air outlet. The centrifugal fan also includes an impeller mounted for rotation about a rotational axis within the volute housing. The impeller has a plurality of fan blades. The plurality of fan blades has an outer surface. The centrifugal fan further includes a light source. The method includes coating or sintering a photocatalyst layer on the inner surface of the volute housing and the outer surface of the plurality of fan blades. The method also includes emitting light, by the light source, on the photocatalyst layer.

BRIEF DESCRIPTION OF THE DRAWINGS

References are made to the accompanying drawings that form a part of this disclosure and which illustrate the embodiments in which systems and methods described in this specification can be practiced.

Like reference numbers represent like parts throughout.

DETAILED DESCRIPTION

Figure 1A:
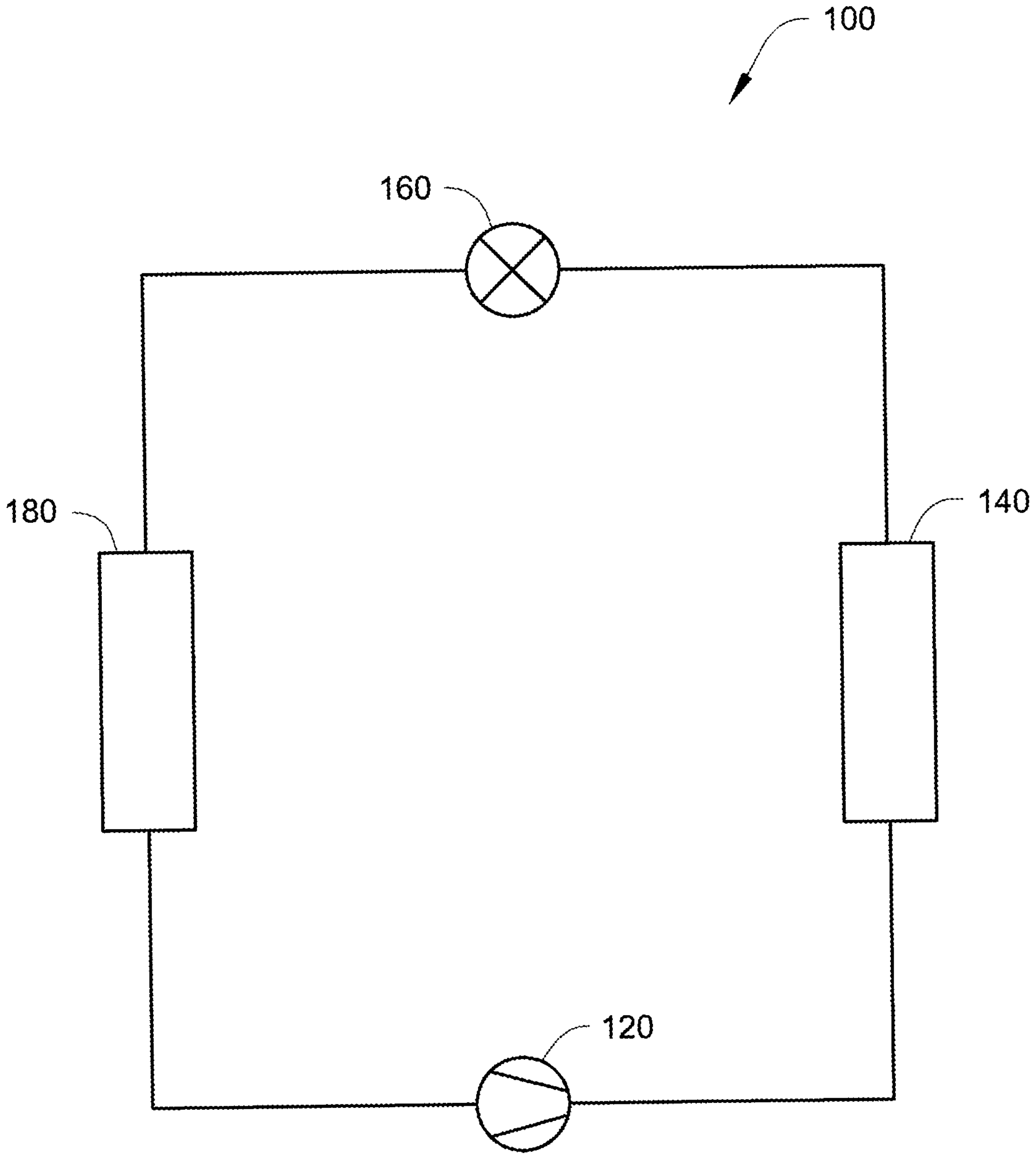
FIG. 1A is a schematic diagram of a refrigeration circuit, which may be implemented in an HVACR system, according to an embodiment.

The following definitions are applicable throughout this disclosure. As defined herein, the term "photocatalyst" may refer to a material which absorbs light to bring the material to a higher energy level and provides such energy to a reacting substance to make a chemical reaction occur. It will be appreciated that in catalyzed photolysis, light is absorbed by an adsorbed substrate. In photo-generated catalysis, the photocatalytic activity depends on the ability of the catalyst to create electron-hole pairs, which generate free radicals (e.g. hydroxyl radicals: OH) able to undergo secondary reactions. It will also be appreciated that the practical application was made possible by the discovery of e.g., water electrolysis by means of e.g., titanium dioxide ($TiO_2$). It will be appreciated that photons have a certain energy. When irradiated on certain substances (such as semiconductors including $TiO_2$), the electrons of the atoms will jump from the valence band to the conduction band after absorbing certain energy. There will be a positively charged hole, that is, photo-generated electrons and photo-generated holes. Positively charged holes combine with water molecules in the air to produce hydroxyl radicals that have the ability to oxidize and decompose, while negative electrons combine with oxygen in the air to form active oxygen. Because such electrons and holes have strong reducing and oxidizing properties, respectively, so they can make the substances on the semiconductor undergo an oxidation-reduction reaction (e.g., to reduce/kill pathogens), thereby converting light energy into chemical energy. These substances are called photocatalysts.

As defined herein, the term "ultraviolet" or "UV" may refer to a form of electromagnetic radiation with a wavelength ranges from at or about 10 nm to at or about 400 nm. As defined herein, the term "UVA" may refer to UV with a wavelength ranges from at or about 315 nm to at or about 400 nm, the term "UVB" may refer to UV with a wavelength ranges from at or about 280 nm to at or about 315 nm, and the term "UVC" may refer to UV with a wavelength ranges from at or about 100 nm to at or about 280 nm.

Particular embodiments of the present disclosure are described herein with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In this description, as well as in the drawings, like-referenced numbers represent elements that may perform the same, similar, or equivalent functions.

Additionally, the present disclosure may be described herein in terms of functional block components, code listings, optional selections, page displays, and various processing steps. It should be appreciated that such functional blocks may be realized by any number of hardware and/or software components configured to perform the specified functions. For example, the present disclosure may employ various integrated circuit components, e.g., memory elements, processing elements, logic elements, look-up tables, and the like, which may carry out a variety of functions under the control of one or more microprocessors or other control devices.

The scope of the disclosure should be determined by the appended claims and their legal equivalents, rather than by the examples given herein. For example, the steps recited in any method claims may be executed in any order and are not limited to the order presented in the claims. Moreover, no element is essential to the practice of the disclosure unless specifically described herein as "critical" or "essential."

FIG. 1A is a schematic diagram of a refrigerant circuit 100, according to an embodiment. The refrigerant circuit 100 generally includes a compressor 120, a condenser 140, an expansion device 160, and an evaporator 180. An "expansion device" as described herein may also be referred to as an expander. In an embodiment, the expander may be an expansion valve, expansion plate, expansion vessel, orifice, or the like, or other such types of expansion mechanisms. It should be appreciated that the expander may be any suitable type of expander used in the field for expanding a working fluid to cause the working fluid to decrease in pressure and temperature. In an embodiment, the evaporator 180 can be a microchannel heat exchanger. The refrigerant circuit 100 is an example and can be modified to include additional components. For example, in an embodiment, the refrigerant circuit 100 can include other components such as, but not limited to, an economizer heat exchanger, one or more flow control devices, a receiver tank, a dryer, a suction-liquid heat exchanger, or the like.

The refrigerant circuit 100 can generally be applied in a variety of systems used to control an environmental condition (e.g., temperature, humidity, air quality, or the like) in a space (generally referred to as a conditioned space). Examples of such systems include, but are not limited to, HVACR systems, transport refrigeration systems, or the like. In an embodiment, a HVACR system can be a rooftop unit or a heat pump air-conditioning unit.

The compressor 120, condenser 140, expansion device 160, and evaporator 180 are fluidly connected. In an embodiment, the refrigerant circuit 100 can be configured to be a cooling system (e.g., an air conditioning system) capable of operating in a cooling mode. In an embodiment, the refrigerant circuit 100 can be configured to be a heat pump system that can operate in both a cooling mode and a heating/defrost mode. A centrifugal fan (not shown, described later) can be provided to a heat exchanger such as the condenser 140 and/or the evaporator 180.

It will be appreciated that the centrifugal fans are disclosed in e.g., the U.S. Pat. Nos. 7,591,633; 7,186,080; 7,108,478; 5,570,996; 5,558,499; 3,627,440; 3,307,776; 3,217,976; 2,981,461; 2,951,630; 2,798,658; 2,727,680;

3,221,983; and 1,862,523, the entire disclosure of which are hereby incorporated by reference herein.

The refrigerant circuit 100 can operate according to generally known principles. The refrigerant circuit 100 can be configured to heat and/or cool a liquid process fluid (e.g., a heat transfer fluid or medium (e.g., a liquid such as, but not limited to, water or the like)), in which case the refrigerant circuit 100 may be generally representative of a liquid chiller system. The refrigerant circuit 100 can alternatively be configured to heat and/or cool a gaseous process fluid (e.g., a heat transfer medium or fluid (e.g., a gas such as, but not limited to, air or the like)), in which case the refrigerant circuit 100 may be generally representative of an air conditioner and/or heat pump.

In operation, the compressor 120 compresses a working fluid (e.g., a heat transfer fluid (e.g., refrigerant or the like)) from a relatively lower pressure gas to a relatively higher-pressure gas. The relatively higher-pressure gas is also at a relatively higher temperature, which is discharged from the compressor 120 and flows through the condenser 140. In accordance with generally known principles, the working fluid flows through the condenser 140 and rejects heat to the process fluid (e.g., water, air, etc.), thereby cooling the working fluid. The cooled working fluid, which is now in a liquid form, flows to the expansion device 160. The expansion device 160 reduces the pressure of the working fluid. As a result, a portion of the working fluid is converted to a gaseous form. The working fluid, which is now in a mixed liquid and gaseous form flows to the evaporator 180. The working fluid flows through the evaporator 180 and absorbs heat from the process fluid (e.g., a heat transfer medium (e.g., water, air, etc.)), heating the working fluid, and converting it to a gaseous form. The gaseous working fluid then returns to the compressor 120. The above-described process continues while the heat transfer circuit is operating, for example, in a cooling mode (e.g., while the compressor 120 is enabled).

Figure 1B:
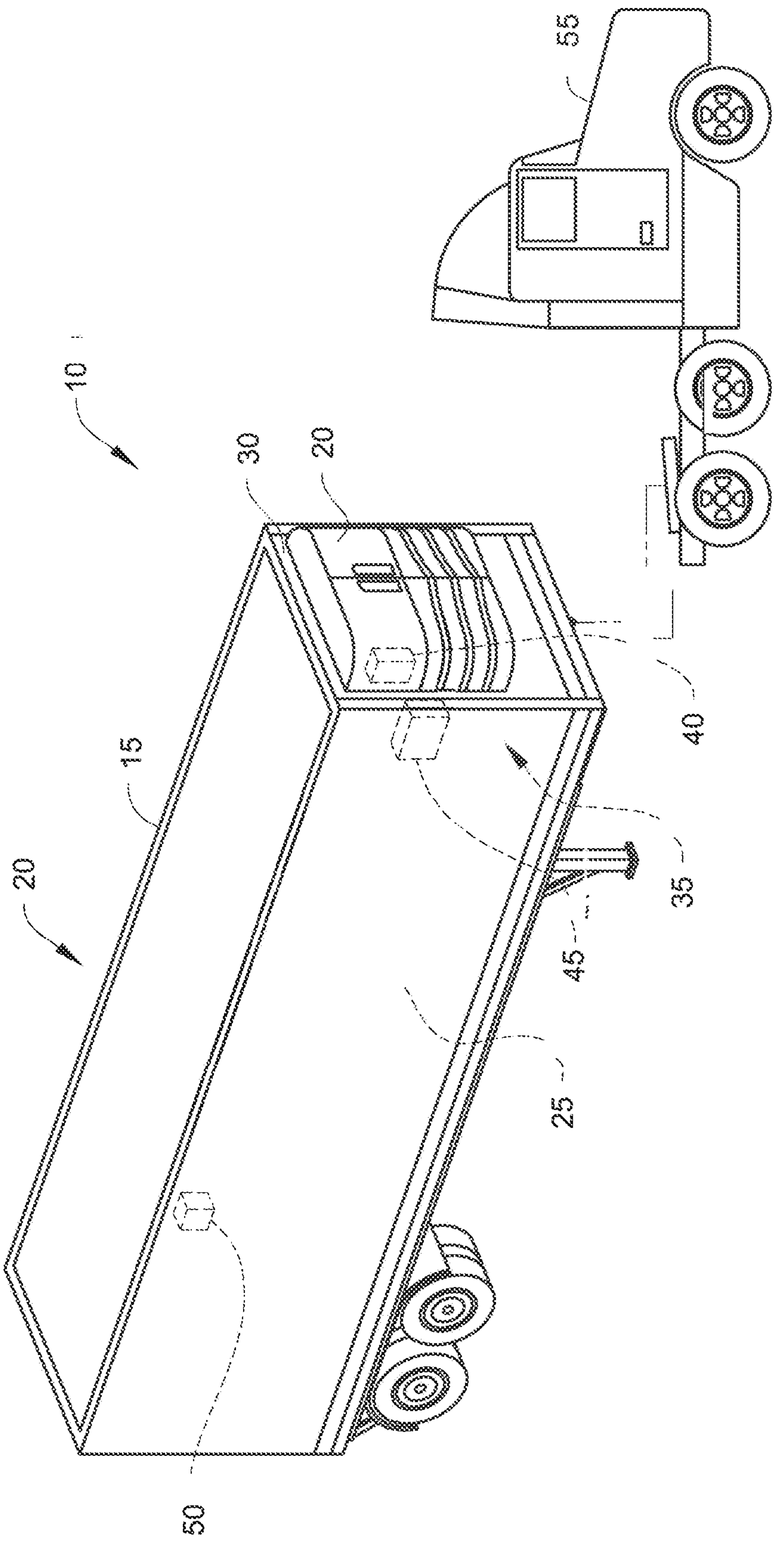
FIG. 1B is a perspective view of a climate controlled transport unit, according to an embodiment.

FIG. 1B is a perspective view of a climate controlled transport unit 20 attachable to a tractor 55, according to an embodiment. The climate controlled transport unit 20 includes a transport climate control system 10 for a transport unit 15. The tractor 55 is attached to and is configured to tow the transport unit 15. The transport unit 15 shown in FIG. 1B is a trailer.

The transport climate control system 10 includes a climate control unit (CCU) 20 that provides environmental control (e.g. temperature, humidity, air quality, etc.) within a climate controlled space 25 of the transport unit 15. The CCU 20 is disposed on a front wall 30 of the transport unit 15. In other embodiments, it will be appreciated that the CCU 20 can be disposed, for example, on a rooftop or another wall of the transport unit 15. The CCU 20 includes a climate control circuit (see e.g., FIG. 1A) that connects, for example, a compressor, a condenser, an evaporator, and an expansion device to provide conditioned air within the climate controlled space 25. In an embodiment, the CCU 20 can be a transport refrigeration unit.

The transport climate control system 10 also includes a programmable climate controller 35 and one or more sensors (not shown) that are configured to measure one or more parameters of the transport climate control system 10 (e.g., an ambient temperature outside of the transport unit 15, an ambient humidity outside of the transport unit 15, a compressor suction pressure, a compressor discharge pressure, a supply air temperature of air supplied by the CCU 20 into the climate controlled space 25, a return air temperature of air returned from the climate controlled space 25 back to the CCU 20, a humidity within the climate controlled space 25, etc.) and communicate climate control data to the climate controller 35. It will be appreciated that a supply fan or blower (e.g., a centrifugal fan or blower, not shown, see 600 of FIG. 5 and blower 358 of FIG. 1C) can be positioned close to a transport unit air outlet and configured to supply air to the climate controlled space 25. It will be appreciated that the centrifugal fan is also disclosed in application U.S. 2010/0120345A1 which is also hereby incorporated by reference in its entirety. The one or more climate control sensors can be positioned at various locations outside the transport unit 20 and/or inside the transport unit 20 (including within the climate controlled space 25).

The climate controller 35 is configured to control operation of the transport climate control system 10 including components of the climate control circuit. The climate controller 35 may include a single integrated control unit 40 or may include a distributed network of climate controller elements 40, 45. The number of distributed control elements in a given network can depend upon the particular application of the principles described herein. The measured parameters obtained by the one or more climate control sensors can be used by the climate controller 35 to control operation of the climate control system 10.

The climate controlled transport unit 20 includes an independent sensor 50. In the illustrated embodiment, the independent sensor 50 is represented as a single sensor. It will be appreciated that in other embodiments, the climate controlled transport unit 20 can include a plurality of independent sensors 50. In some embodiments, the independent sensor 50 is a dedicated regulatory sensor that can provide independent verification of climate control parameters (e.g., temperature, humidity, atmosphere, etc.) within the climate controlled space 25. The independent sensor 50 is not used by the climate controller 35 to control operation of the transport climate control system 10. The independent sensor 50 is in electronic communication with a power source (not shown) of the CCU 20. In an embodiment, the independent sensor 50 is in electronic communication with the climate controller 35. It will be appreciated that the electronic communication between the independent sensor 50 and the climate controller 35 can enable network communication of the sensed verification values or parameters (e.g., temperature data of cargo stored in the climate controlled space 300) measured by the independent sensor 50. The electronic communication between the climate controller 35 and the independent sensor 50 does not enable the sensed verification values or parameters to be utilized in a control of the CCU 20.

Figure 1C:
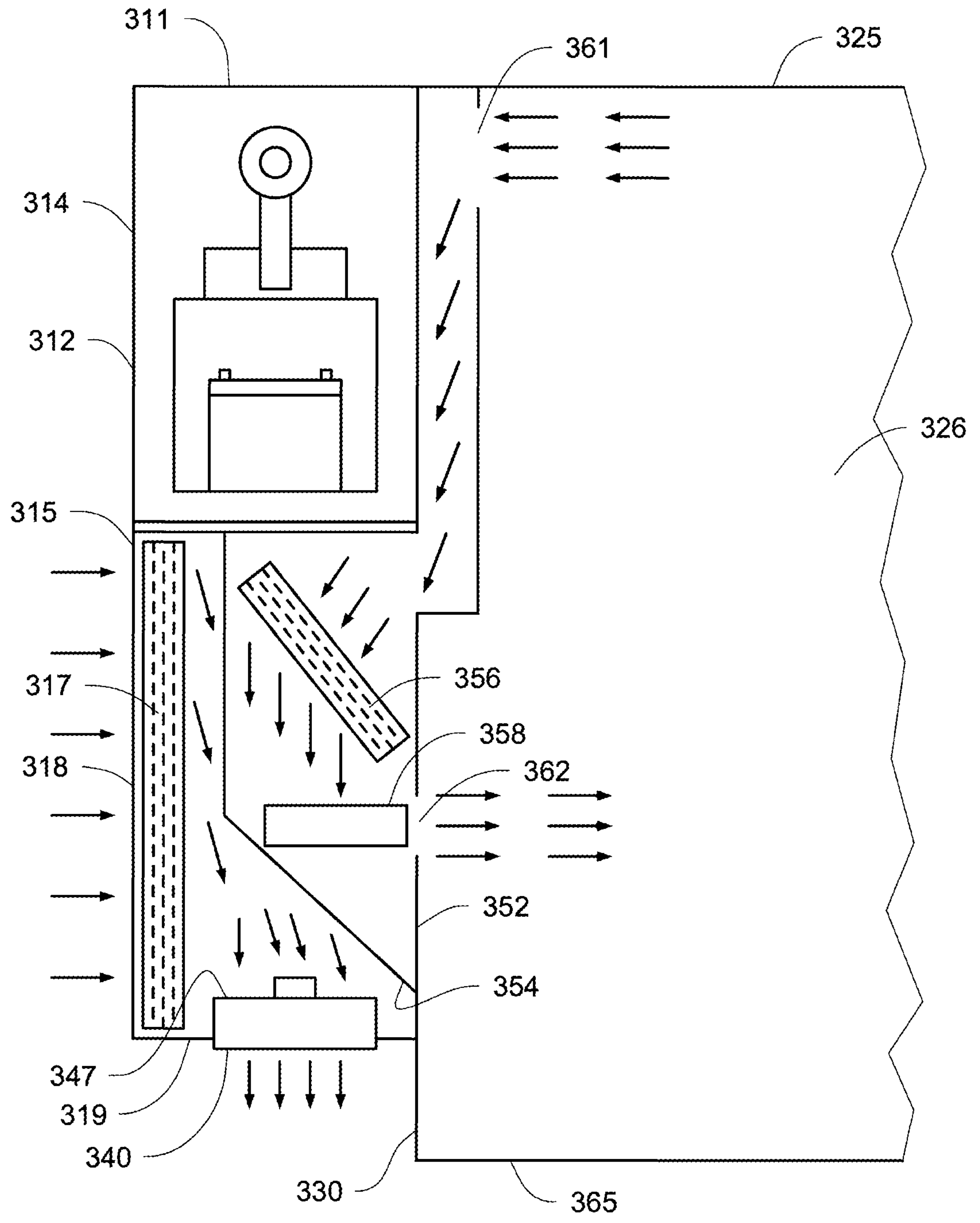
FIG. 1C illustrates a side schematic view of the climate controlled transport unit of FIG. 1B, according to an embodiment.

FIG. 1C illustrates a side schematic view of the climate controlled transport unit of FIG. 1B, according to an embodiment. The climate controlled transport unit (CCTU) 311 includes a housing 312. Inside the housing 312 of the CCTU 311, an upper compartment 314 is generally positioned above a condenser compartment 315.

The upper compartment 314 can be configured to contain a plurality of components of the CCTU 311 including, for example, a compressor, an engine, a battery, an air filter and/or a muffler. The condenser compartment 315 can contain a condenser 317. A plurality of fans 340 are installed at a bottom portion 319 of the condenser compartment 315. Each of the fans 340 has an inlet that is generally located inside the condenser compartment 315 and an outlet that is generally located outside of the condenser compartment 315. A guard 318 of the condenser compartment 315 has apertures to allow air to get inside the condenser compartment 315. In some embodiments, the engine is a diesel engine. The condenser 317 is positioned in a front part of the condenser compartment 315 behind the guard 318. The condenser compartment 315 also includes the fan 347 that is installed at the bottom portion 319.

The CCTU 311 also includes an evaporator compartment 352 that is generally positioned behind the condenser compartment 315. The condenser compartment 315 and the evaporator compartment 352 are separated by a partition 354. As illustrated, both of the condenser compartment 315 and the evaporator compartment 352 are generally positioned in a lower part of the housing 312 of the CCTU 311 in relation to the upper compartment 314.

The CCTU 311 is configured to be attached on a front wall 330 of a transport unit 325. The evaporator compartment 352 is configured to have a transport unit air inlet 361 and a transport unit outlet 362 in communication with an inner space 326 of the transport unit 325. A blower 358 (e.g., a centrifugal fan, see also 600 of FIG. 5) is positioned close to the transport unit air outlet 362. An evaporator 356 is positioned in an airflow passage formed by the transport unit air inlet 361, the blower 358 and the transport unit air outlet 362. The transport unit air inlet 361 is generally positioned above the transport unit air outlet 362. In the illustrated embodiment, the blower 358 is positioned lower than the evaporator 356 in the evaporator compartment 352.

The arrows in FIG. 1C indicate airflow directions. In operation, the airflow generated by the fans 340 is generally sucked into the condenser compartment 315 through the apertures of the guards 318. The airflow then passes through the condenser 317 and flows out of the condenser compartment 315 through the fans 340 at the bottom portion 319. The airflow is blown in a downward direction toward a bottom 365 of the transport unit 325 by the fans 340. It is to be noted that the upper compartment 314 is generally not positioned within the airflow generated by the fans 340.

In the evaporator compartment 352, airflow generated by the operation of the blower 358 is generally sucked into the evaporator compartment 352 from the transport unit air inlet 361 and then passes through the evaporator 356. The airflow is then driven out of the transport unit air outlet 362 by the blower 358.

It is to be noted that the condenser 317, the fans 340, the evaporator 356 and the blower 362 are all configured to be positioned close to the bottom portion 319 of the CCTU 311 in relation to the upper compartment 314. By positioning the condenser 317, the fans 340, the evaporator 356 and the blower 358 generally below the upper compartment 314, the upper compartment 314 can have relatively more room to accommodate components of the CCTU 311 without increasing a profile of the CCTU 311. The upper compartment 314 is generally isolated from the airflow generated by the operation of the fans 340 and/or the blower 358.

Generally, the upper compartment 314, which is configured to accommodate components such as the engine and the compressor, can have a raised temperature in operation due to heat generated by the components. Isolating the upper compartment 314 from the evaporator compartment 352 that is configured to accommodate the evaporator 356 can help shield the heat generated by, for example, the engine and/or the compressor, away from the evaporator 356.

Figure 1D:
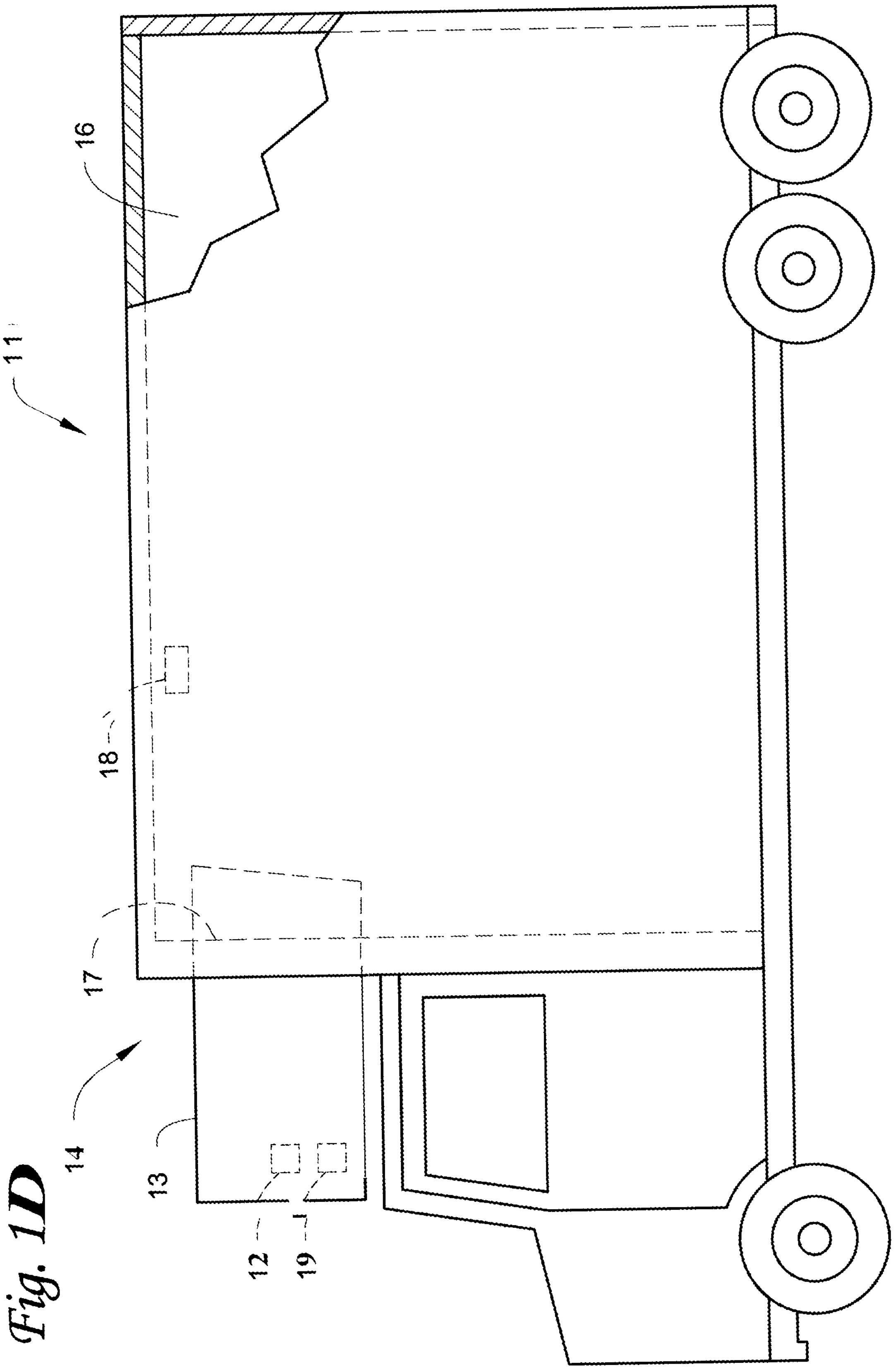
FIG. 1D is a side view of a truck with a transport climate control system, according to an embodiment.

FIG. 1D is a side view of a truck 11 with a transport climate control system 14, according to an embodiment. FIG. 1D depicts the climate-controlled straight truck 11 that includes the climate controlled space 16 for carrying cargo and the transport climate control system 14.

The transport climate control system 14 includes a climate control unit (CCU) 13 that is mounted to a front wall 17 of the climate controlled space 16. The CCU 13 can include, among other components, a climate control circuit (see, e.g., FIG. 1A) that connects, for example, a compressor, a condenser, an evaporator, and an expansion device to provide climate control within the climate controlled space 16. In an embodiment, the CCU 13 can be a transport refrigeration unit.

The transport climate control system 14 also includes a programmable climate controller 19 and one or more climate control sensors (not shown) that are configured to measure one or more parameters of the transport climate control system 14 (e.g., an ambient temperature outside of the truck 11, an ambient humidity outside of the truck 11, a compressor suction pressure, a compressor discharge pressure, a supply air temperature of air supplied by the CCU 13 into the climate controlled space 16, a return air temperature of air returned from the climate controlled space 16 back to the CCU 13, a humidity within the climate controlled space 16, etc.) and communicate climate control data to the climate controller 19. It will be appreciated that a supply fan or blower (e.g., a centrifugal fan or blower, not shown, see 600 of FIG. 5 and blower 358 of FIG. 1C) can be positioned close to a transport unit air outlet on the wall 17 and configured to supply air to the climate controlled space 16 through the transport unit air outlet. It will be appreciated that the centrifugal fan is also disclosed in application U.S. 2010/0120345A1. The one or more climate control sensors can be positioned at various locations outside the truck 11 and/or inside the truck 11 (including within the climate controlled space 16).

The climate controller 19 is configured to control operation of the transport climate control system 14 including components of the climate control circuit. The climate controller 19 may include a single integrated control unit 19 or may include a distributed network of climate controller elements 19, 12. The number of distributed control elements in a given network can depend upon the particular application of the principles described herein. The measured parameters obtained by the one or more climate control sensors can be used by the climate controller 19 to control operation of the climate control system 14.

The truck 11 includes an independent sensor 18. In the illustrated embodiment, the independent sensor 18 is represented as a single sensor. It will be appreciated that in other embodiments, the truck 11 includes a plurality of independent sensors 18. In some embodiments, the independent sensor 18 is a dedicated regulatory sensor that can provide independent verification of climate control parameters (e.g., temperature, humidity, atmosphere, etc.) within the climate controlled space 16. The independent sensor 18 is not used by the climate controller 19 to control operation of the transport climate control system 14. The independent sensor 18 is in electronic communication with a power source (not shown) of the CCU 13. In an embodiment, the independent sensor 18 is in electronic communication with the climate controller 19. It will be appreciated that the electronic communication between the independent sensor 18 and the climate controller 19 can enable network communication of the sensed verification values or parameters (e.g., temperature data of cargo stored in the climate controlled space 16) measured by the independent sensor 18. The electronic communication between the climate controller 19 and the independent sensor 18 does not enable the sensed verification values or parameters to be utilized in a control of the CCU 13.

Figure 2:
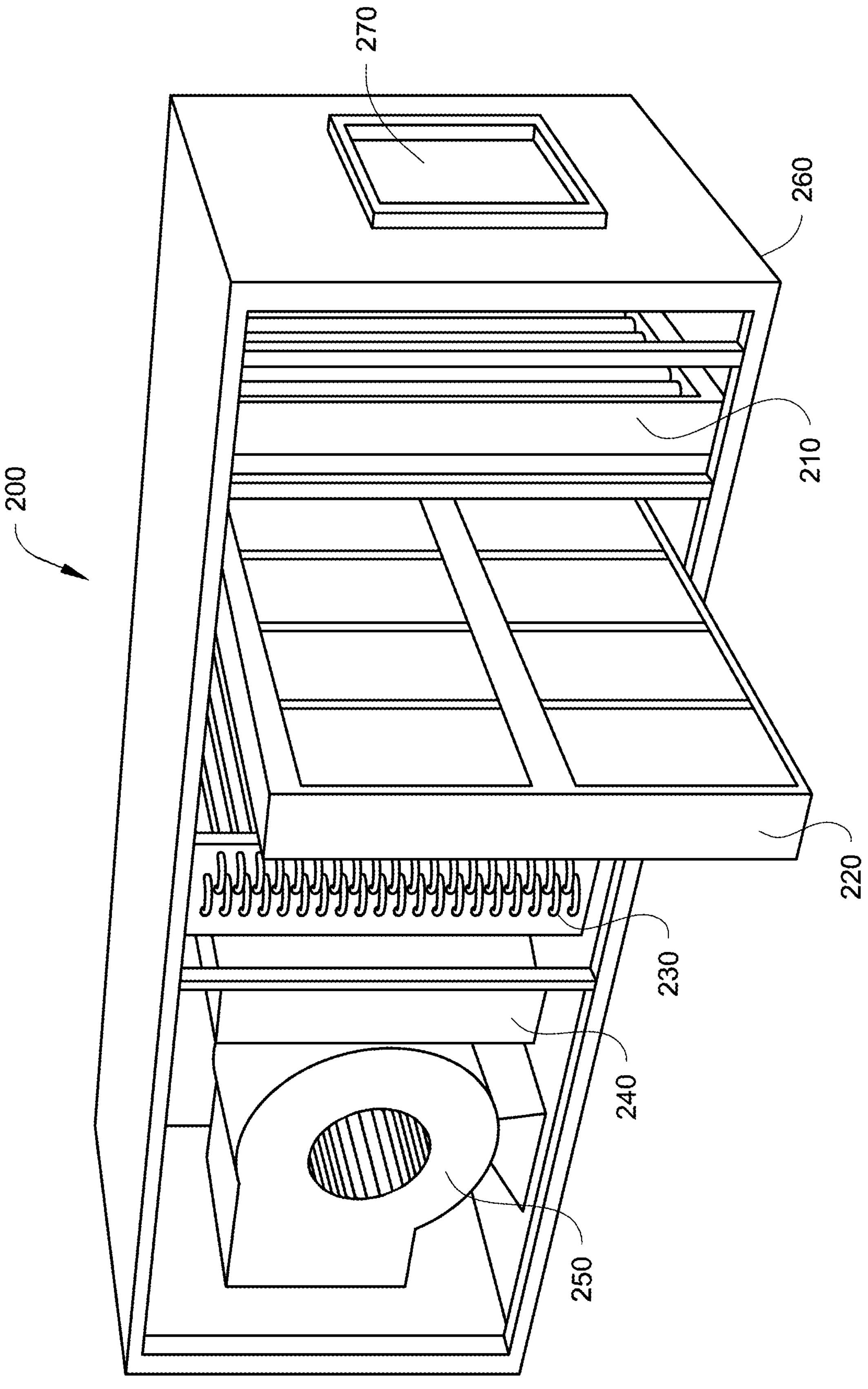
FIG. 2 is a perspective view, partially cutaway, illustrating an air handling unit of an HVACR system having a centrifugal fan, according to an embodiment.

FIG. 2 is a perspective view, partially cutaway, illustrating an air handling unit (air handler) 200 of an HVACR system having a centrifugal fan 250, according to an embodiment.

The unit 200 includes an enclosure 260. In one embodiment, the enclosure 260 can be a generally rectangular cabinet having a first end wall defining an air inlet opening 270 (to allow air to flow into an internal space of the enclosure 260) and a second end wall defining an air outlet opening (not shown, to allow air to flow out of the enclosure 260 via an air outlet (that overlaps with the air outlet opening) of the centrifugal fan 250, see e.g., 660 in FIG. 5). In FIG. 2, a side wall of the enclosure 260 is cutaway and the internal space of the enclosure 260 is shown.

The unit 200 also includes a primary filter 210 and a secondary filter 220. In one embodiment, the primary filter 210 and the secondary filter 220 can be one filter. It will be appreciated that the primary filter 210 and/or the secondary filter 220 can be a porous device configured to remove impurities or solid particles from air flow passed through the device.

In one embodiment, outer surface(s) (e.g., the entire surface facing the airflow and/or the entire surface opposite to the surface facing the airflow) of the secondary filter 220 (and/or the primary filter 210) can be covered (or coated or sintered) with e.g., a photocatalyst layer (see FIGS. 16A-16D). A light source (not shown, see FIGS. 10A-15A) can be added in the enclosure 260 to emit light on the photocatalyst layer disposed on the outer surface(s) of the filter where the air passes through. This embodiment provides a solution to achieve photocatalytic oxidation and/or ultraviolet germicidal irradiation on surfaces of the filter(s). In this embodiment, more space is needed (e.g., for disposing the light source) in the enclosure 260 (and thus a length of the enclosure may need to be increased, or the space of other components within the enclosure 260 may be occupied by the light source), air pressure drop may occur (e.g., due to the added resistance to the air because of the added photocatalyst layer to the filter) on the outer surface(s) of the filter, and/or a sealed installation may be needed (e.g., for the light source to prevent e.g., UV light such as UVC light from being leaked out from the enclosure 260). In this embodiment, the efficiency and efficacy of one-time filtration and/or sterilization of air can be optimal because e.g., the outer surface(s) of the filter may cover the entire airflow passing through the filter.

The unit 200 further includes a component (e.g., a coil) 230. In one embodiment, the component 230 can be an air conditioning evaporator coil disposed in the flow path of air passing from the air inlet opening 270 to the air outlet opening of the enclosure 260 (which is also the air outlet of the fan 250). It will be appreciated that the component 230 can be different types in that the working fluid can be e.g., refrigerant, water, or the like. For example, when the working fluid is refrigerant, the component 230 can be an evaporator coil for cooling, and/or can be a condenser coil for heating. For example, when the working fluid is water, the component 230 can be tube(s) for chilled water to go through for cooling, and can be tube(s) for hot water to go through for heating.

The unit 200 also includes a humidifier 240 configured to add moisture to the air to prevent dryness that can cause irritation in many parts of the human body or to increase humidity in the air.

Also the unit 200 includes a fan (or blower) 250. In one embodiment, the fan 250 can be a centrifugal fan having electric drive motor (not shown) to drive the fan 250 (e.g., to drive a shaft of the fan 250, see FIG. 11A, to rotate the impeller of the fan 250). It will be appreciated that a centrifugal fan is a mechanical device for moving air or other gases toward the outlet of the fan in a direction at an angle (e.g., perpendicular) to the incoming air from the inlet of the fan. A centrifugal fan often contains a ducted housing to direct outgoing air in a specific direction or across a heat sink. The centrifugal fan can increase the speed and volume of an air stream with rotating impellers.

Figure 3:
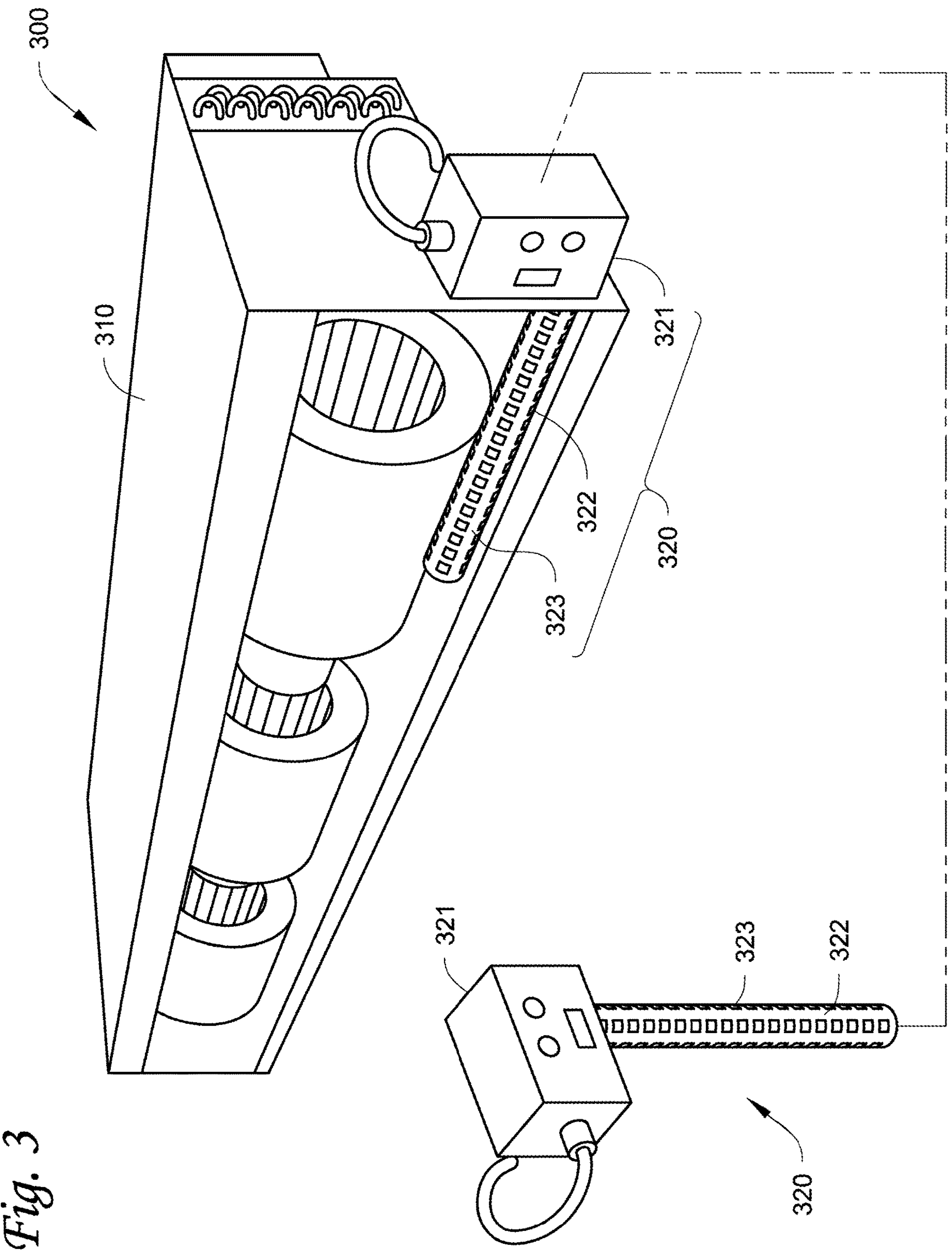
FIG. 3 is a perspective view illustrating a return air box of an HVACR system having a light source, according to an embodiment.

FIG. 3 is a perspective view illustrating a return air box 300 of an HVACR system having a light source 320, according to an embodiment. The box 300 includes an enclosure 310. In FIG. 3, viewed from a return air outlet of the enclosure 310, the internal space of the enclosure 310 is shown.

The light source 320 includes a lamp 322 and a controller 321. In one embodiment, the controller 321 can be a control gear and/or a ballast. The lamp 322 can be the light source described in FIGS. 10A-15A. In one embodiment, the lamp 322 is covered by a shell 323 (e.g., made of metal net, sponge, etc.) having a photocatalyst layer (see FIGS. 16A-16D). The lamp 322 can emit light on the shell. This embodiment provides a solution (e.g., photocatalytic oxidation and/or ultraviolet germicidal irradiation) similar to the one described in detail for the centrifugal fan 250. In this embodiment, the light source 320 is inserted into the internal space of the enclosure, the installation is easy, the cost is low, and there is low resistance to the airflow. In this embodiment, the efficacy and/or efficiency of one-time filtration and/or sterilization of air may not be optimal because the entire airflow passing through the box 300 may not be covered/contacted by the solution (e.g., photocatalytic oxidation and/or ultraviolet germicidal irradiation) provided by the shell of the lamp 322 and from the lamp 322.

Figure 4:
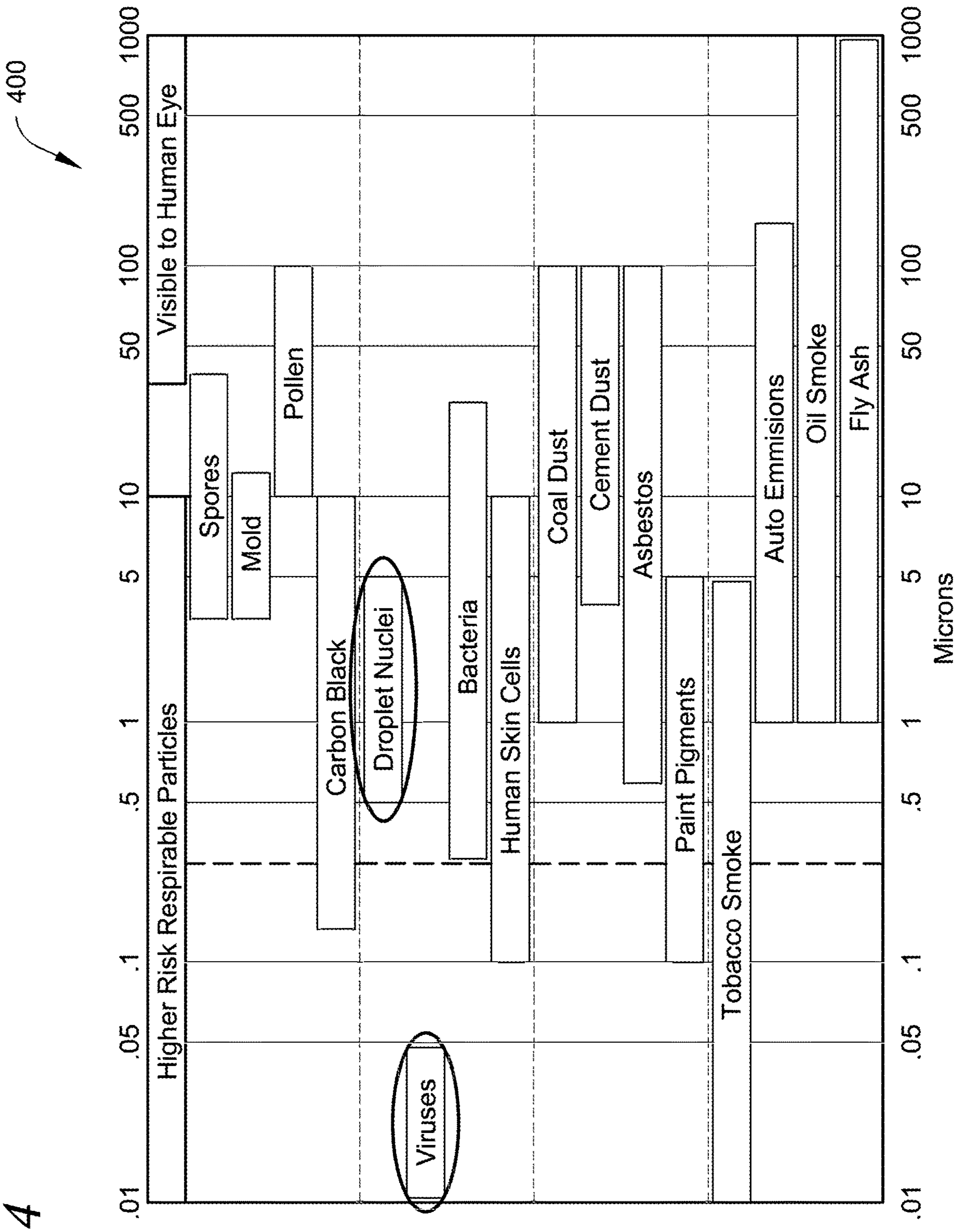
FIG. 4 is a table showing sizes of particles, according to an embodiment.

FIG. 4 is a table 400 showing sizes of particles, according to an embodiment. As shown in FIG. 4, viruses have a size ranging from at or about 0.01 microns to at or about 0.05 microns, droplet nuclei have a size ranging from at or about 0.5 microns to at or about 5 microns. Many high risk respirable particles have a size ranging from at or about 0.01 microns to at or about 10 microns. Particles having a size at or about 50 microns or larger are typically visible to human eyes. It will be appreciated that computational fluid dynamics analysis results can demonstrate efficiency of removing high risk respirable particles (e.g., having a size ranging from at or about 0.01 microns to at or about 10 microns). Efficiency differences between a centrifugal airflow and a whirl airflow can show that the centrifugal airflow has higher efficiency than the whirl airflow for removing high risk respirable particles. Such efficiency differences can be achieved by, e.g., a centrifugal fan throwing the high risk respirable particles to the walls of the centrifugal fan via airflow, and thus the particles may drop from the air, especially for respirable particles having smaller size.

Figure 5:
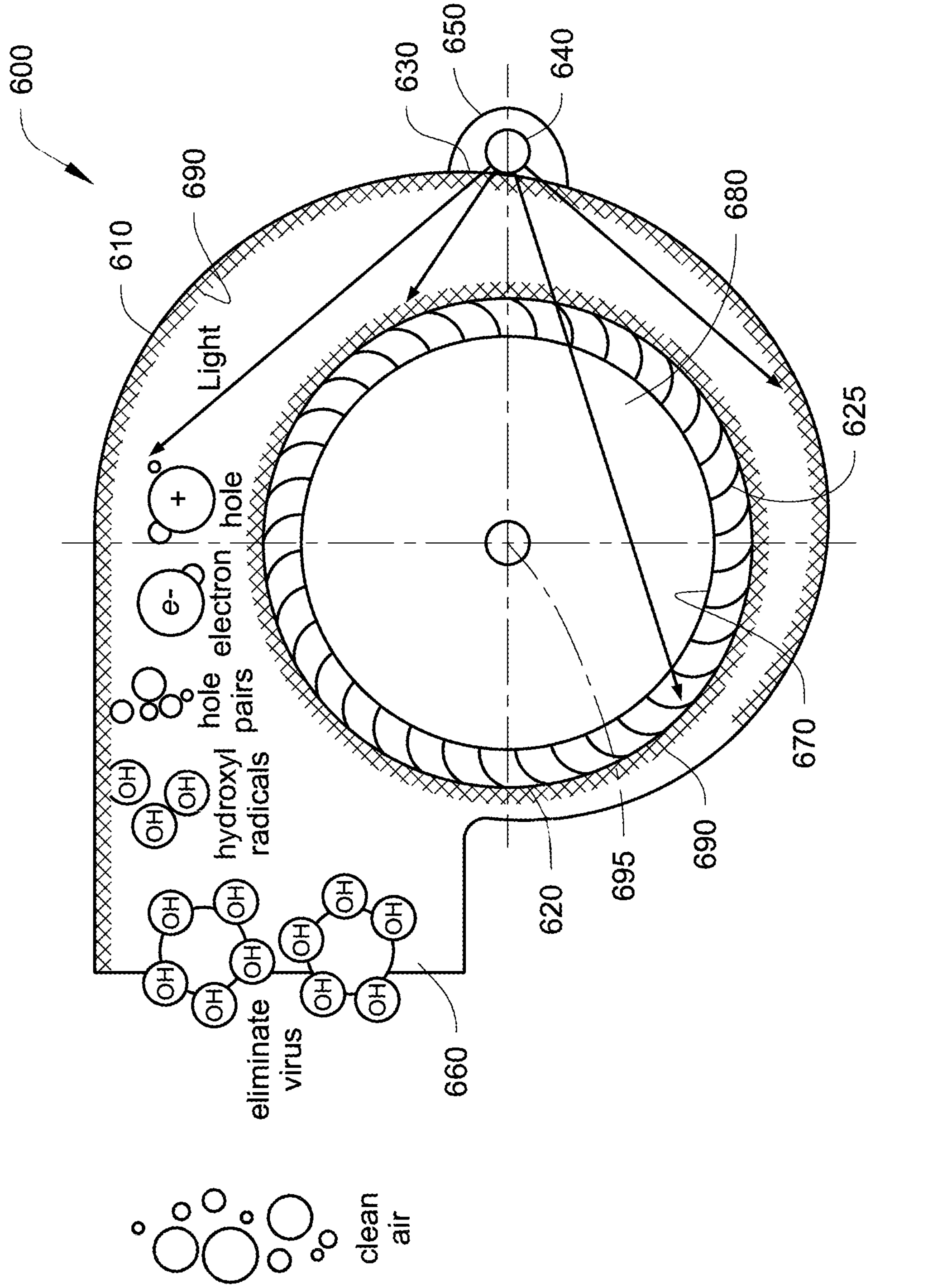
FIG. 5 is a side schematic view of a centrifugal fan for an HVACR system, according to an embodiment.

FIG. 5 is a side schematic view of a centrifugal fan 600 for an HVACR system, according to an embodiment. It will be appreciated that the centrifugal fan 600 can be used as the centrifugal fan/blower of the systems described in FIGS. 1A-1D and FIG. 2. The centrifugal fan 600 includes a volute housing 610 having an inner surface and a curved inlet shroud 670. It will be appreciated that the centrifugal fan 600 can be a direct drive fan or a pulley drive fan. It will also be appreciated that in an embodiment, the centrifugal fan 600 can be a volute-less fan (see FIG. 6) without the volute housing 610. The volute housing 610 defines an air outlet 660. The curved inlet shroud 670 defines an air inlet 680. The air inlet 680 has an inlet airflow cross-sectional area that lies substantially perpendicular to an outlet airflow cross-sectional area of the air outlet 660. In such embodiment, air or other gases can flow into the air inlet 680 (e.g., in a direction into the paper) and then flow out of the air outlet 660 in a direction (e.g., to the left of the paper) perpendicular to the direction of the air entering the air inlet 680.

The centrifugal fan 600 also includes an impeller 620 mounted for rotation about a rotational axis 695 within the volute housing 610. The impeller 620 has a plurality of fan blades 625. The plurality of fan blades 625 has an outer surface.

The centrifugal fan 600 further includes a light source 640 disposed at a first end of the centrifugal fan 600 opposite to a second end (where the air outlet 660 locates) of the centrifugal fan 600. The centrifugal fan 600 includes a window 630 and a reflector 650 that covers the window 630. The light source 640 is enclosed by the window 630 and the reflector 650. It will be appreciated that the window 630 is part of the volute housing 610 so that the shape of the volute housing 610 is unchanged. The centrifugal fan 600 includes a photocatalyst layer 690 disposed on the inner surface of the volute housing 610 and the outer surface of the impeller 620 including outer surface of the plurality of fan blades 625. It will be appreciated that although a small number of fan blades 625 are shown in FIG. 5, persons skilled in the art would appreciate the structure of the impeller including a full set of fan blades arranged around the circumference of the impeller 620. It will also be appreciated that in FIG. 5, the photocatalyst layer 690 disposed on the outer surface of the impeller 620 is for illustrative purpose. In an embodiment, the photocatalyst layer 690 is disposed on the outer surface of the impeller 620 including outer surface of the plurality of fan blades 625. See also FIGS. 10A and 10B for the details of the embodiment of FIG. 5.

FIG. 5 shows how light (e.g., UVA, UVB, UVC, visible light, etc.) emitted from the light source 640 interacts with the photocatalyst layer 690 to remove/reduce pathogens from the air. Embodiments provided herein can provide a high efficiency solution to provide a purification product with an all airflow treatment to remove or reduce pathogens (virus, bacteria, etc.) without air pressure drop (i.e., adding no extra resistance to the airflow), without changing the shape of the volute housing (and thus the characteristics (such as the airflow, the noise, etc.) of the centrifugal fan are unchanged), and without requiring extra space.

Figure 6:
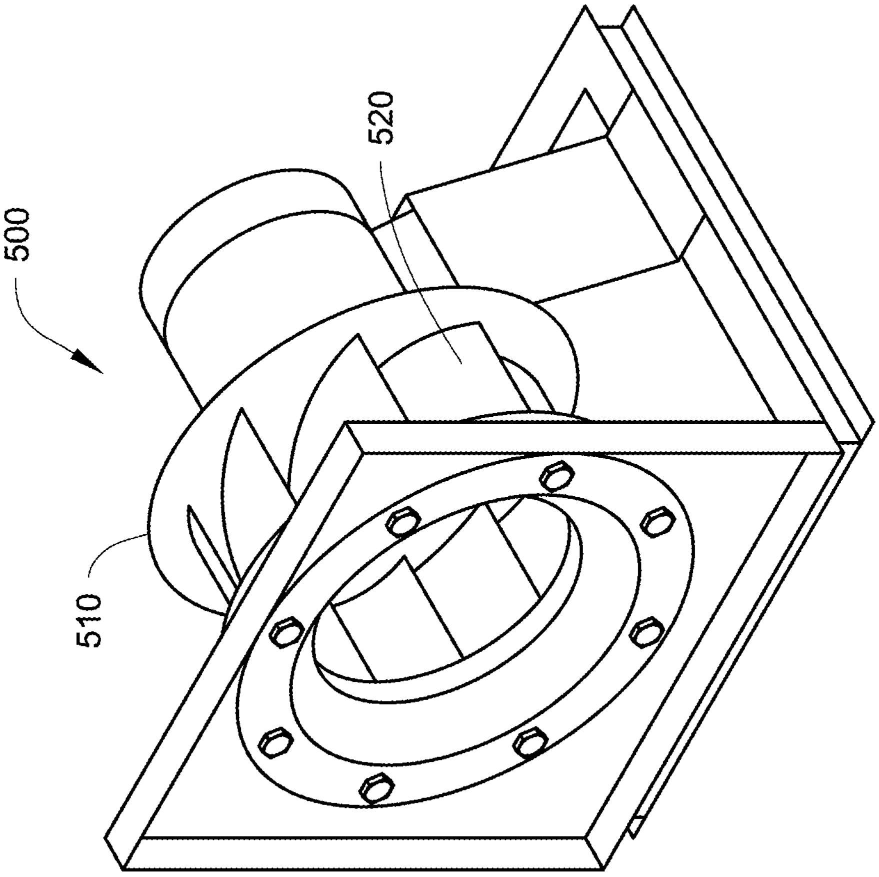
FIG. 6 is a perspective view of a volute-less centrifugal fan for an HVACR system, according to an embodiment.

FIG. 6 is a perspective view of a volute-less centrifugal fan 500 for an HVACR system, according to an embodiment. The fan 500 includes an impeller 510 having a plurality of fan blades 520. The fan 500 also includes a photocatalyst layer (not shown, see e.g., 690 of FIG. 5) disposed on an outer surface of the impeller 510 including an outer surface of the blades 520. In an embodiment, the photocatalyst layer can be on an inner surface of a fan section panel (not shown) of the fan 500. A light source (not shown, see e.g., 640 of FIG. 5) can be disposed at an appropriate location so that light (e.g., UVA, UVB, UVC, visible light, etc.) emitted from the light source can interact with and fully cover the photocatalyst layer to remove/reduce pathogens from the air.

Figure 7:
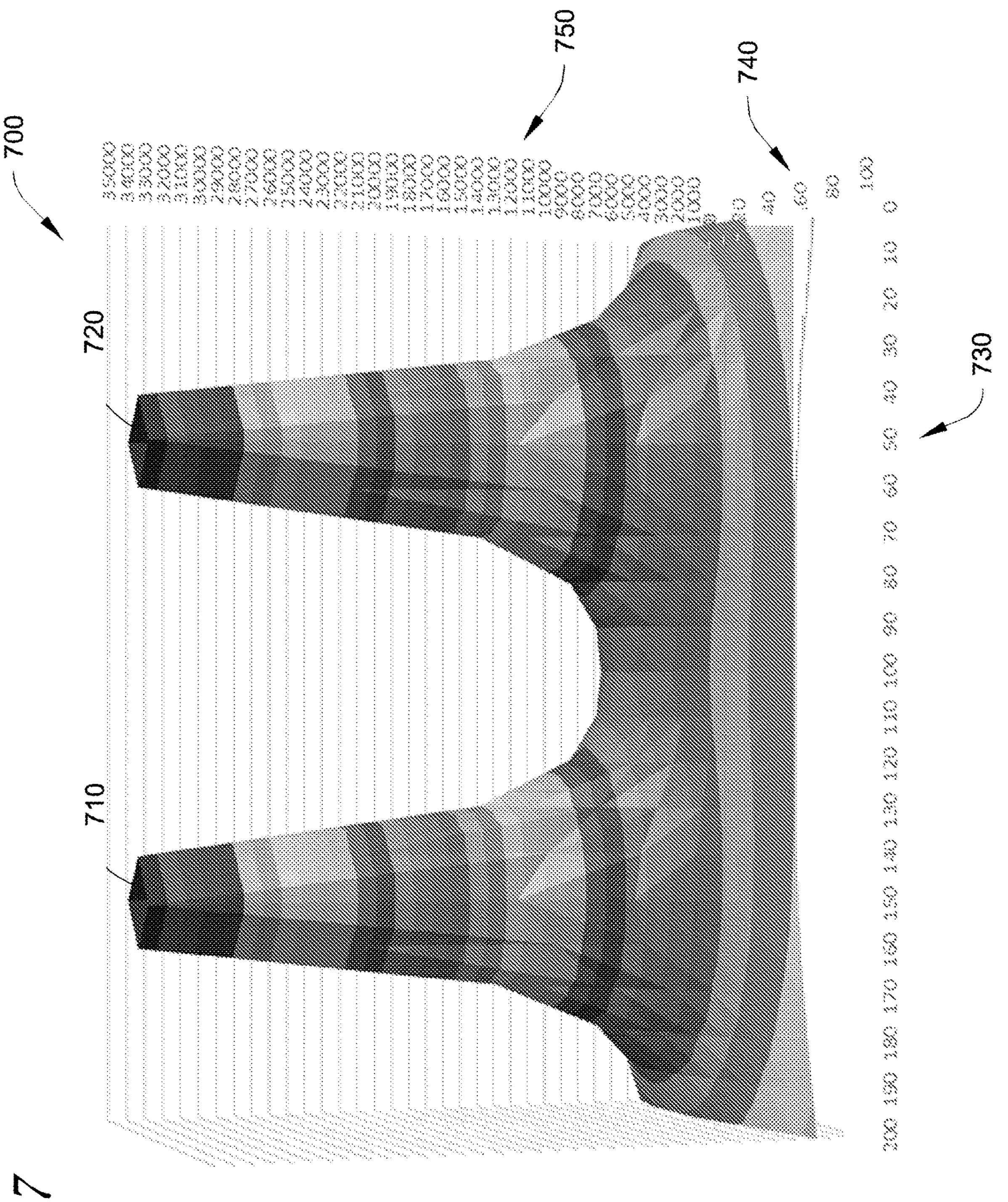
FIG. 7 illustrates simulation results of light intensity of two light sources in a centrifugal fan, according to an embodiment.

FIG. 7 illustrates simulation results 700 of light intensity of two light sources (e.g., two elongated lamp) in a centrifugal fan (e.g., a PCO centrifugal fan), according to an embodiment. In the simulation, two 10 watts UVC light sources are simulated. Each of the light source is similar to the light source of FIGS. 13A and 13B (described later, where each light source extends from an end of the light source connecting the power source to a tip of the light source in a length direction). In FIG. 7, the unit of the UVC light intensity is microwatts per centimeter$^2$. The coordinates 730 and 740 represent the size (unit millimeter) of the air outlet of the centrifugal fan (e.g., substantially rectangular). The coordinates 750 represent the light intensity. It is shown in FIG. 7 that along each of the elongated UVC lamp in a length direction of the lamp, the intensity (710 and 720) is decreased (toward the tip of the lamp) or increased (away from the tip of the lamp). It will be appreciated that FIG. 7 demonstrates the importance of the location (and thus the light intensity for inactivating virus) of the light source(s). Embodiments disclosed herein can achieve optimal location (and thus light intensity) with desired air coverage.

Figure 8:
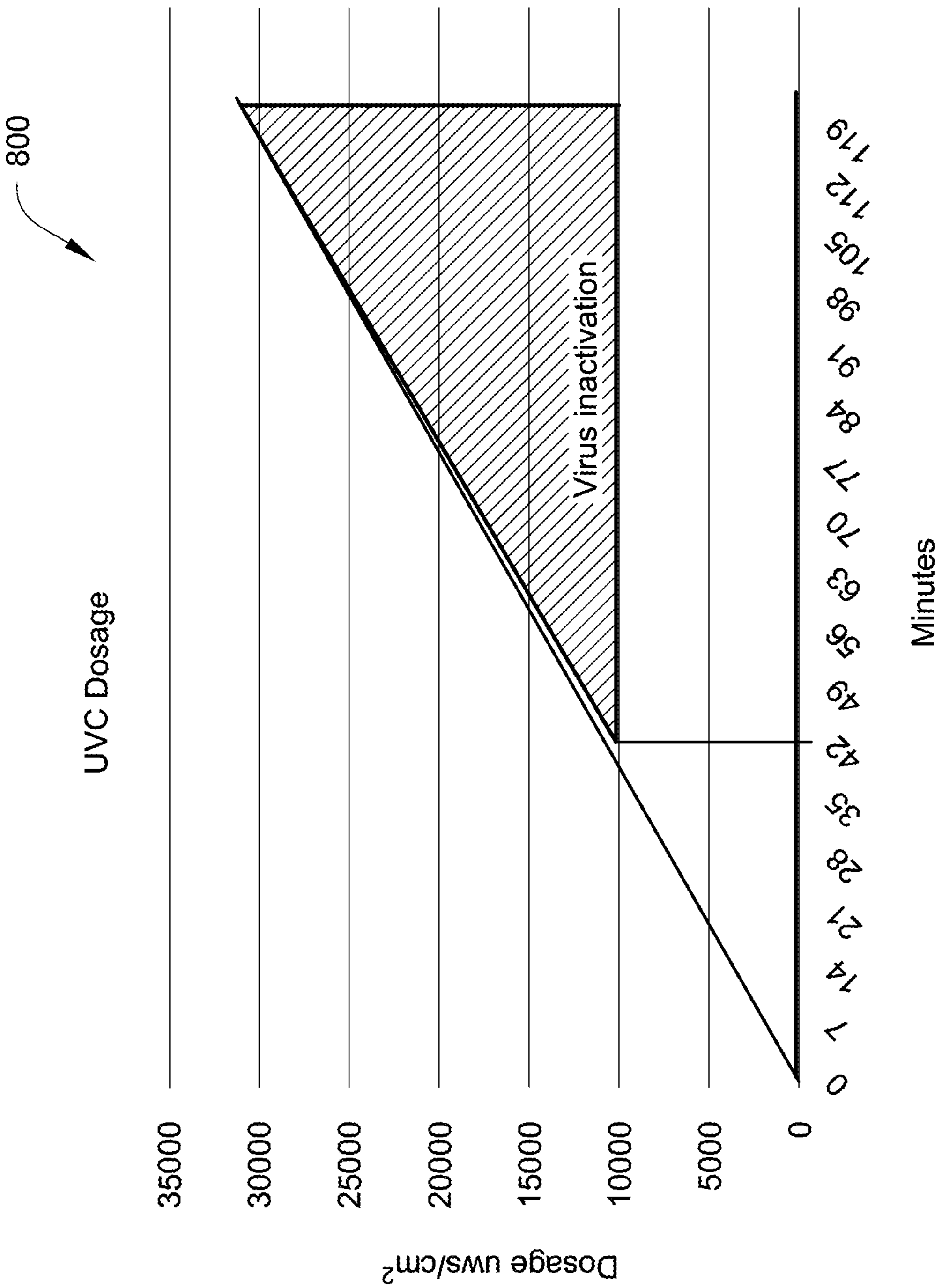
FIG. 8 illustrates simulation results of time and light dosage needed to inactivate virus in a centrifugal fan, according to an embodiment.

FIG. 8 illustrates simulation results 800 of time and light dosage needed to inactivate pathogens (e.g., virus) in a centrifugal fan, according to an embodiment. In the simulation for FIG. 8, airflow rate at or about 500 meter$^3$/hour is deployed, the chamber (internal space for airflow to pass through) size of the centrifugal fan is at or about 30 meter$^3$. As shown in FIG. 8, the minimum UVC dosage to inactivate the lipophilic virus (all or almost all virus) in the centrifugal fan is at or about 10,000 (microwatts second per centimeter$^2$), and the minimum time to reach the minimum UVC dosage to inactivate the virus (all or almost all virus) in the centrifugal fan is at or about 42 minutes. It will be appreciated that FIG. 8 demonstrates the importance of the light intensity (and thus the location) of the light source(s) with respect to time. The bigger the light intensity, more virus are inactivated during a given time. Embodiments disclosed herein can achieve optimal light intensity with desired air coverage.

Figures 9A, 9B:
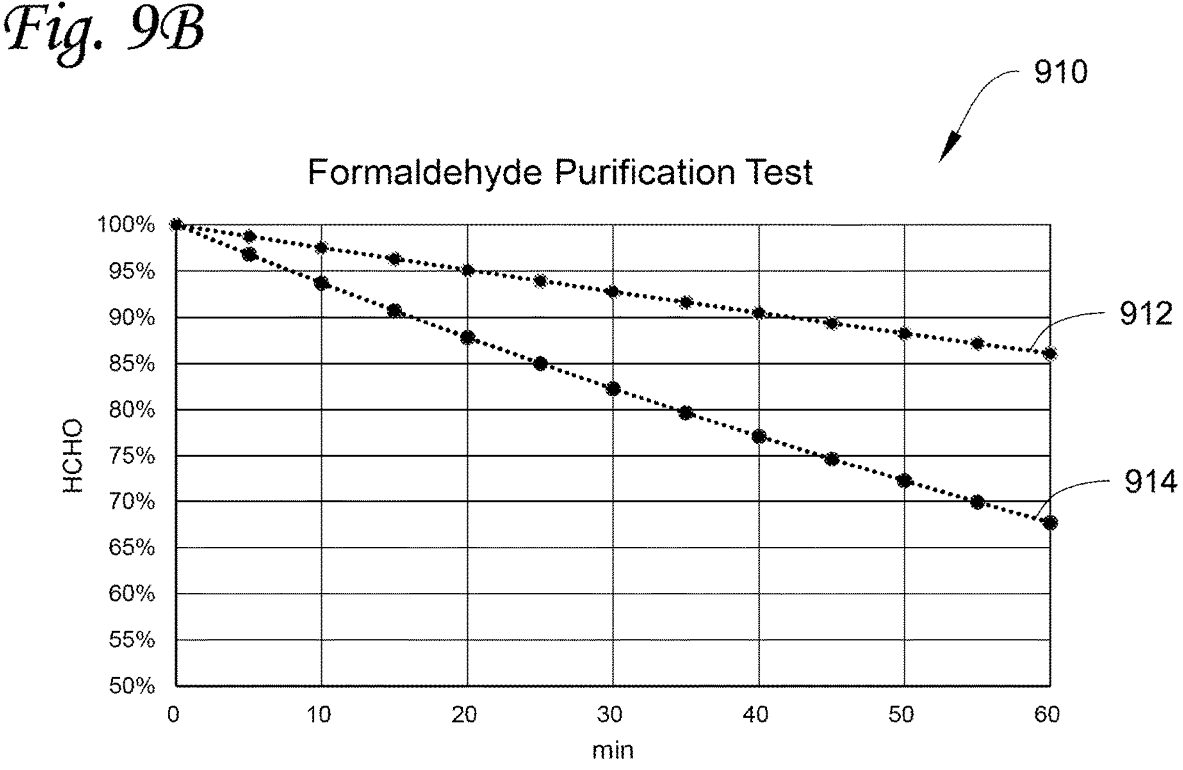
FIG. 9A illustrates test results of noise and airflow changes in a centrifugal fan, according to an embodiment.
FIG. 9B illustrates test results of a formaldehyde purification test, according to an embodiment.

FIG. 9A illustrates test results 900 of noise and airflow changes in a centrifugal fan, according to an embodiment. In FIG. 9A, the column "Baseline" represents the baseline values (without any light source) of noise, input power (in watts), and the airflow (in cubic meter per hour at 12 pascal). The column "1 lamp/fan" represents the values (with one light source) of noise, input power (in watts), and the airflow (in cubic meter per hour at 12 pascal) relative to the baseline values. The column "2 lamps/fan" represents the values (with two light sources) of noise, input power (in watts), and the airflow (in cubic meter per hour at 12 pascal) relative to the baseline values.

As shown in FIG. 9A, with one light source (see e.g. the light source in FIGS. 13A and 13B) being added into the centrifugal fan, the noise in the centrifugal fan is increased by at or about 1.2 dB relative to the baseline value, and the airflow in the chamber of the centrifugal fan is decreased by at or about 3% (because the light source occupies the space, and thus the airflow is reduced) relative to the baseline value. With two light sources (see e.g. the light source in FIGS. 13A and 13B) being added into the centrifugal fan, the noise in the centrifugal fan is increased by at or about 1.3 dB relative to the baseline value, and the airflow in the chamber of the centrifugal fan is decreased by at or about 8% (because the light sources occupy the space and thus the airflow is reduced) relative to the baseline value. FIG. 9A shows that embodiments disclosed herein do not significantly increase the noise and/or decrease the airflow, and users can choose different configurations (e.g., one lamp or two lamps) based on the users' requirements such as noise, airflow, light intensity, etc.

FIG. 9B illustrates test results 910 of a formaldehyde purification test, according to an embodiment. It will be appreciated that the light (emitted from the light source) can be emitted on a photocatalyst layer to react with the photocatalyst to generate hydroxyl radicals (which can oxidize airborne biological particles and convert volatile organic compound to $H_2O$ and $CO_2$ to inactivate or kill the pathogens). For example, UVC photons can react with a photocatalyst to create hydroxyl radicals, and hydroxyl radicals can oxidize airborne biological particles and/or convert volatile organic compound to $H_2O$ and $CO_2$. Line 912 shows the formaldehyde purification test results on photocatalytic oxidation plugging in a duct (e.g., box 300 of FIG. 3). Line 914 shows the formaldehyde purification test results on photocatalytic oxidation in a centrifugal fan. FIG. 9B shows that for a given time period, the centrifugal fan configuration can achieve more formaldehyde reduction compared with the duct configuration.

FIGS. 10A-15E are perspective views of a centrifugal fan having light source(s), according to some embodiments. It will be appreciated that the component(s) with the same reference numerals in FIGS. 10A-15E are the same component(s) throughout this disclosure unless otherwise specified.

Figure 10A:
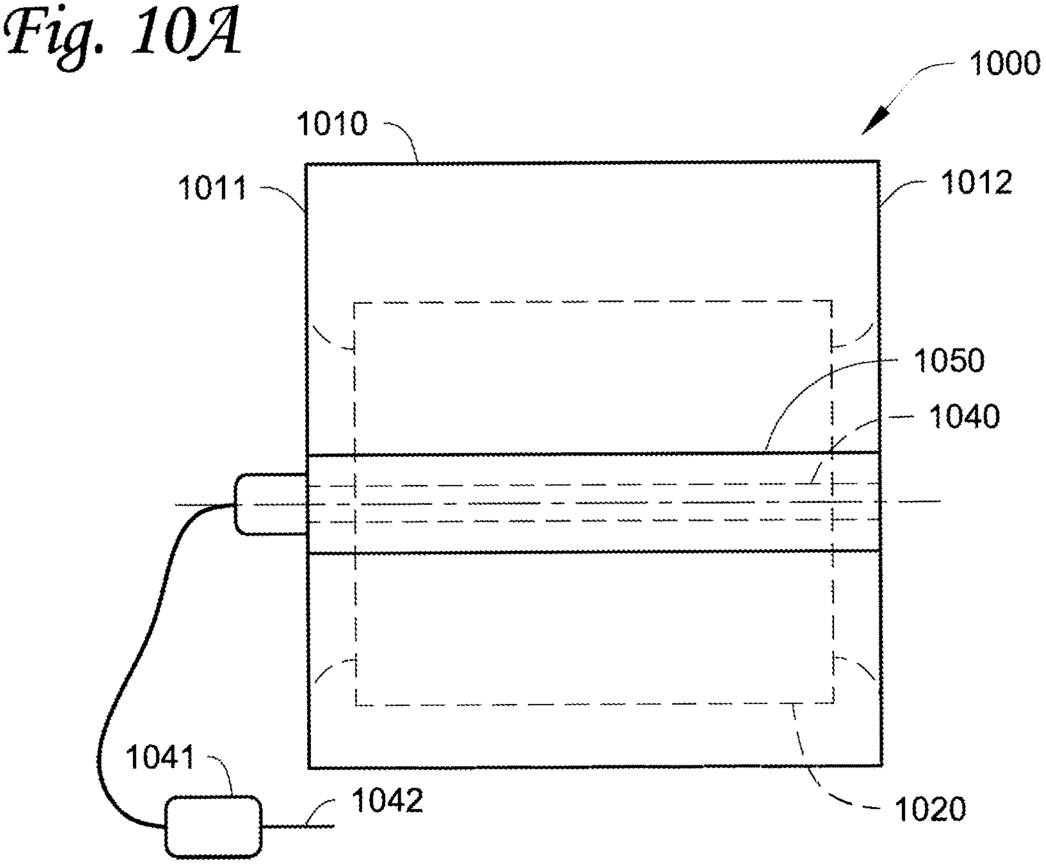
FIGS. 10A-15E are perspective views of a centrifugal fan having light source(s), according to some embodiments.
Figure 10B:
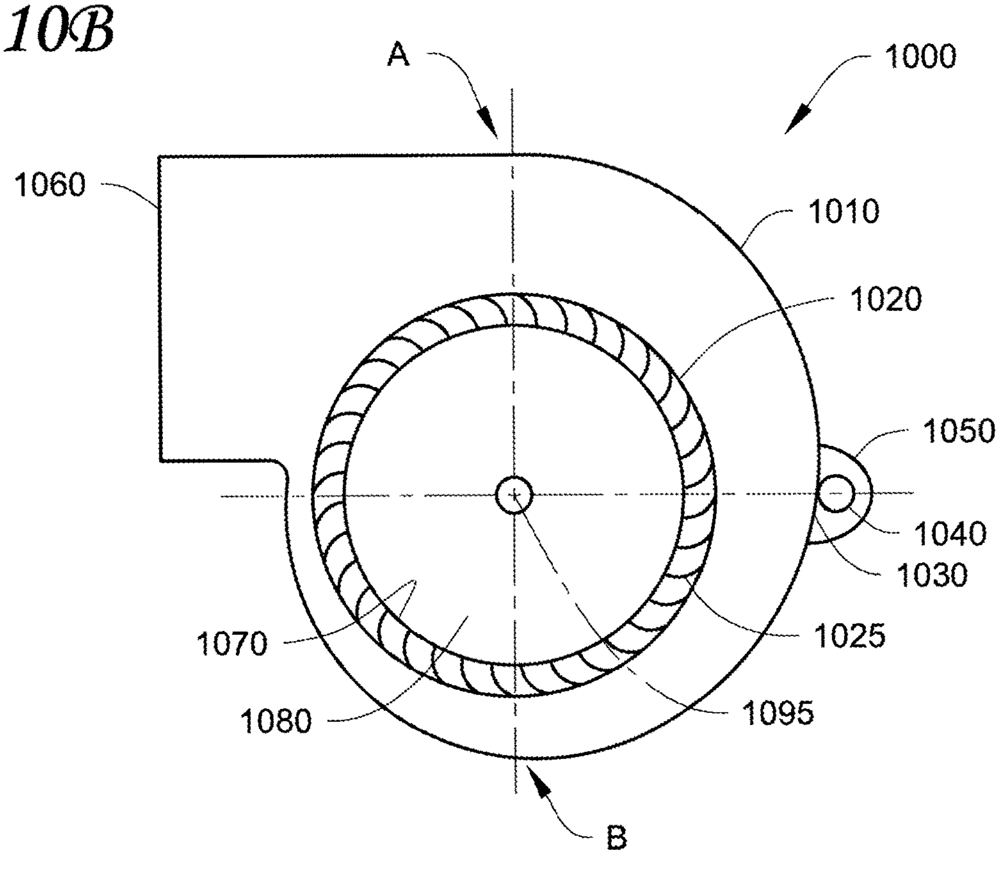

FIGS. 10A and 10B are perspective views of a centrifugal fan 1000 having light source(s), according to an embodiment. FIG. 10A is an end view of the centrifugal fan 1000 and FIG. 10B is a side view of the centrifugal fan 1000.

The centrifugal fan 1000 includes a volute housing 1010 having an inner surface and a curved inlet shroud 1070. The volute housing 1010 defines an air outlet 1060. The curved inlet shroud 1070 defines an air inlet 1080. The air inlet 1080 has an inlet airflow cross-sectional area that lies substantially perpendicular to an outlet airflow cross-sectional area of the air outlet 1060.

The centrifugal fan 1000 also includes an impeller 1020 mounted for rotation about a rotational axis 1095 within the volute housing 1010. The impeller 1020 has a plurality of fan blades 1025. The plurality of fan blades 1025 has an outer surface. The plurality of fan blades 1025 is typically circumferentially spaced, and generally radially outwardly projecting from e.g., the axis 1095.

The centrifugal fan 1000 further includes a light source 1040 disposed at a first end of the centrifugal fan 1000 opposite to a second end (where the air outlet 1060 locates) of the centrifugal fan 1000. The centrifugal fan 1000 includes a window 1030 to allow light to pass through and a reflector 1050 that covers the window 1030 and reflects the light. The light source 1040 is enclosed by the window 1030 and the reflector 1050 and is configured to emit light. In an embodiment, the window 1030 can be part of the volute housing 1010 so that the shape of the volute housing 1010 is unchanged. The centrifugal fan 1000 includes a photocatalyst layer (not shown, see FIG. 5) disposed on the inner surface of the volute housing 1010 and the outer surface of the impeller 1020 including the outer surface of the plurality of fan blades 1025. It will be appreciated that although a small number of fan blades 1025 are shown in FIG. 10B, persons skilled in the art would appreciate the structure of the impeller including a full set of fan blades arranged around the circumference of the impeller 1020. In an embodiment, the photocatalyst layer is disposed on the entire (or almost the entire) inner surface of the volute housing 1010 and the entire (or almost the entire) outer surface of the impeller 1020 including the entire (or almost the entire) outer surface of the plurality of fan blades 1025.

In FIG. 10B, since the window 1030, the light source 1040, and the reflector 1050 are disposed at an end of the centrifugal fan 1000 opposite to the other end of the centrifugal fan 1000 where the air outlet 1060 locates, and since there are spaces between the plurality of fan blades 1025 and that the plurality of fan blades 1025 are rotating during operation, the light source 1040 is able to emit light on the entire (or almost the entire) inner surface of the volute housing 1010 and the entire (or almost the entire) outer surface of the impeller 1020 including the entire (or almost the entire) outer surface of the plurality of fan blades 1025. It will be appreciated that the reflector 1050 can be positioned to achieve desired and/or needed coverage of light (onto the photocatalyst layer), and/or to prevent light (e.g., UV light) leakage.

It will be appreciated that for the light source described herein in all figures, the light source can be of the same type. One light source can include at least one lamp (e.g., at least one mercury lamp or at least one LED lamp). The one light source can also include at least one light-emitting diode light source. The light source can be configured to emit UVA, UVB, UVC, and/or visible light. The light can be emitted e.g., as ultraviolet germicidal irradiation to inactivate or kill the pathogens in the air (e.g., UVC light can kill pathogens in the air directly) or be emitted on the photocatalyst layer to react with the photocatalyst to generate hydroxyl radicals (which can oxidize airborne biological particles and convert volatile organic compound to $H_2O$ and $CO_2$ to inactivate or kill the pathogens). For example, UVC (e.g., having at or about 254 nm wavelength) photons can damage RNA/DNA of cells and viruses. UVC photons can also react with photocatalyst to create hydroxyl radicals, hydroxyl radicals can oxidize airborne biological particles and/or convert volatile organic compound to $H_2O$ and $CO_2$.

In FIG. 10A, the light source 1040, the window 1030, and the reflector 1050 extend from a first side 1011 of the volute housing 1010 to a second side 1012 of the volute housing 1010. In FIGS. 10A and 10B, a portion of the volute housing 1010 is replaced with the window 1030 but the shape of the volute housing 1010 is not changed. That is, the window 1030 is a part of the volute housing 1010. Since the shape of the volute housing 1010 is not changed, the window 1030 does not change the noise and the airflow (see FIG. 9A) in the chamber of the centrifugal fan 1000. In one embodiment, the window 1030 is made of material (e.g., silica glass) with high transmittance of light wavelength for light emitted from light source, to allow UV light to pass through and into an inner space of the volute housing 1010.

In one embodiment, the reflector 1050 has a curved shape. The reflector 1050 can be made of polished aluminum or polished stainless steel or polytetrafluoroethylene to reflect the light emitted from the light source 1040 back into the volute housing 1010 (to e.g., prevent light leaking).

In another embodiment, a set of a light source, a window, and a reflector can be disposed at location A (at the top of the volute housing 1010) and/or location B (at the bottom of the volute housing 1010), respectively. Location A and location B align with the rotational axis 1095 in a vertical direction.

The light source 1040 includes a controller 1041 (e.g., a control gear and/or a ballast) connected to an AC and/or DC power source 1042.

Embodiments disclosed herein do not impact the size and/or length and/or shape of the air handling unit (and/or the centrifugal fan 1000), do not add air-pressure drop (at or about 0 Pa pressure drop), do not add additional resistance to airflow, and provide optimal efficacy and efficiency because all (or almost all) air passing through the air handling unit may pass through the centrifugal fan 1000 (e.g., through the impeller 1020 and the inner space of the volute housing 1010) and thus all (or almost all) air may be treated (e.g., by the photocatalytic oxidation and/or ultraviolet germicidal irradiation solution disclosed herein).

It will be appreciated that virus (such as the COVID-19 virus) typically resides in the droplet nuclei having a size of at or about 0.5 to at or about 5 micrometer (see FIG. 4). The droplet nuclei can be separated to the inner surface of a centrifugal fan by e.g., centrifugal force per the patent application CN108786284A, the entire disclosure of which is hereby incorporated by reference herein. The concentration of droplet nuclei can help to improve the inactivation efficiency of light (e.g., UVC light) and photocatalysis (e.g., the solutions described herein).

Figure 11A:
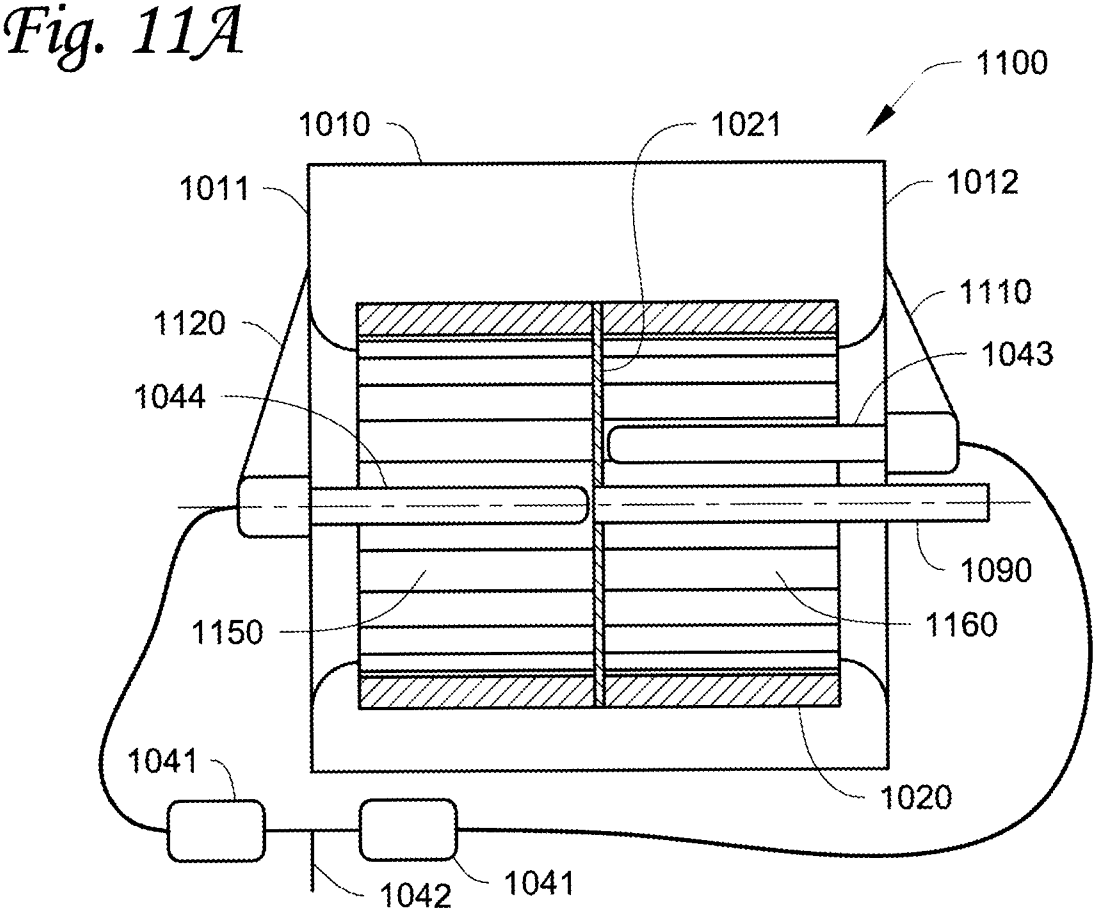
Figure 11B:
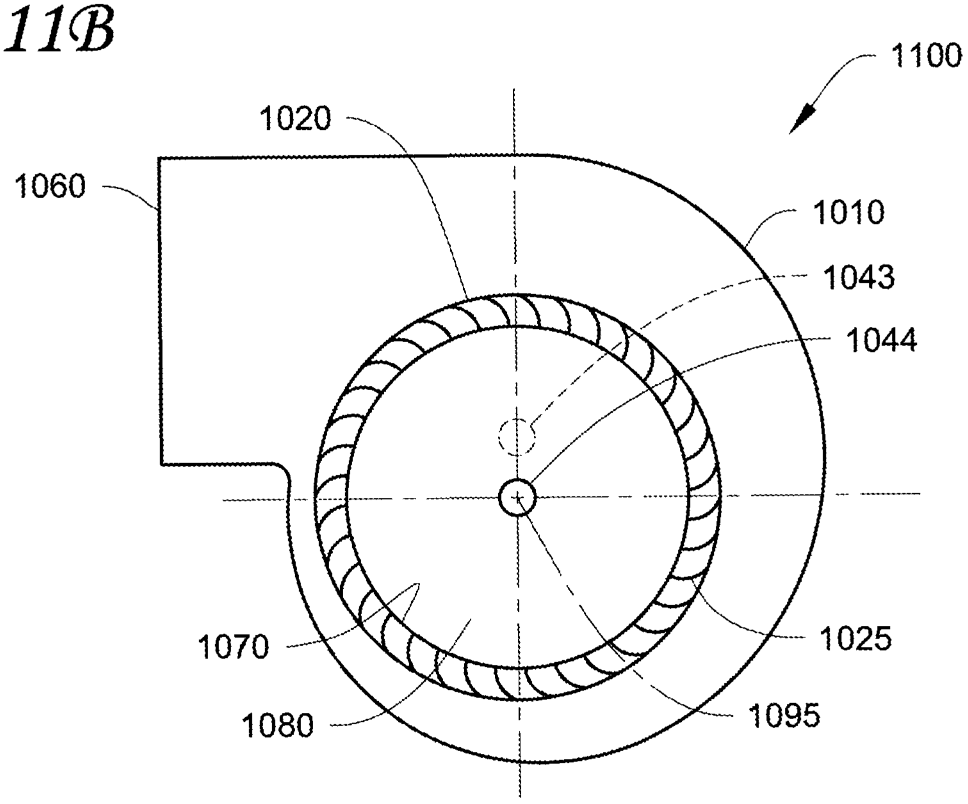
Figure 11C:
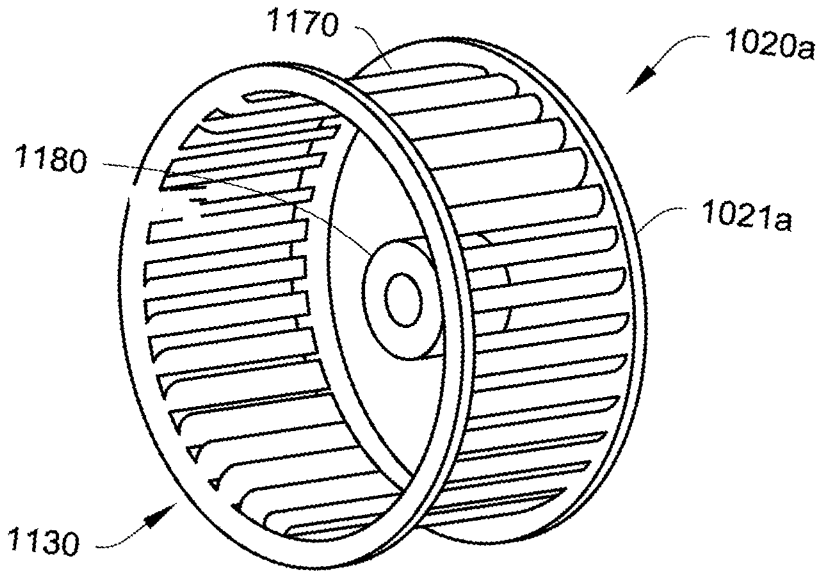
Figure 11D:
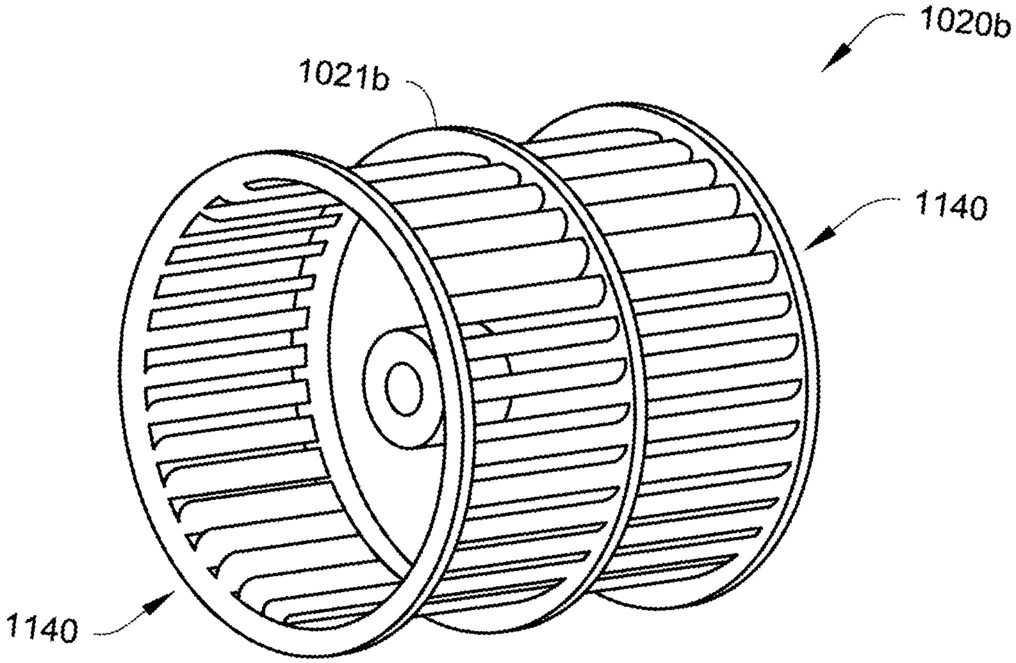

FIGS. 11A and 11B are perspective views of a centrifugal fan 1100 having light source(s), according to an embodiment. FIG. 11A is an end view of the centrifugal fan 1100 and FIG. 11B is a side view of the centrifugal fan 1100. FIGS. 11C and 11D are perspective views of a portion of an impeller having a partition.

The centrifugal fan 1100 includes a shaft 1090 that drives the impeller 1020 to rotate (e.g., by a motor via the shaft 1090). In one embodiment, the shaft 1090 aligns with the rotational axis 1095. The light source(s) 1043, 1044 is/are disposed in an empty space inside the curved inlet shroud 1070 (e.g., at a location on or away from the rotational axis 1095). Brackets (1110, 1120) are provided on the volute housing 1010 to support the light source(s) 1043, 1044. In one embodiment, each of the light source(s) 1043, 1044 can have an H-shape lamp. In an embodiment, the impeller 1020 can have a partition 1021. The light source 1044 extends from a first side 1011 of the volute housing 1010 toward the partition 1021 and an end of the light source 1044 is disposed near the partition 1021 (for better light coverage). The light source 1043 extends from a second side 1012 of the volute housing 1010 toward the partition 1021 and an end of the light source 1043 is disposed near the partition 1021 (for better light coverage). In an embodiment, the partition 1021 separates the chamber (1150 and 1160) of the impeller 1020 into two independent spaces. The partition 1021 may have a disc shape. FIG. 11C is a perspective view of a portion of an impeller **1020*a* having a partition 1021*a*. The partition 1021*a* may have a disc shape and connect a hub boss 1180 and the blade ring 1170 of the impeller 1020*a*. The impeller 1020*a* has a single suction 1130 and the partition 1021*a* is on one side of the impeller 1020*a*. FIG. 11D is a perspective view of a portion of an impeller 1020*b* having a partition 1021*b*. The impeller 1020*b* has double suctions 1140 and the partition 1021*b* is in the middle of the impeller 1020*b***.

Referring back to FIGS. 11A and 11B, the configuration of the light source(s) 1043, 1044 can provide direct light to the airflow and to the photocatalyst layer on the inner surface of the volute housing 1010 and the outer surface of the impeller 1020 including outer surface of the plurality of fan blades 1025.

Figure 12A:
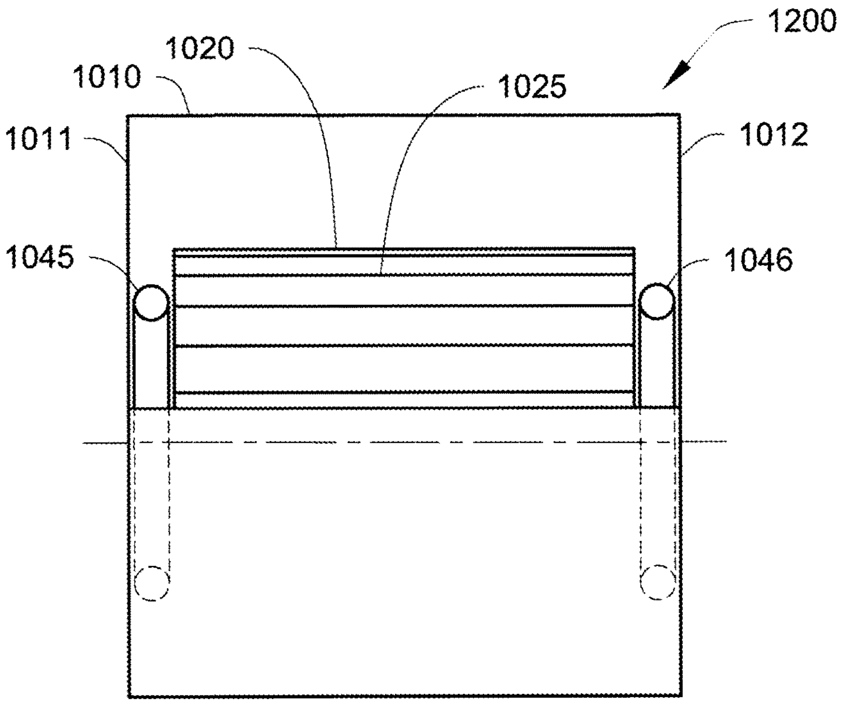
Figure 12B:
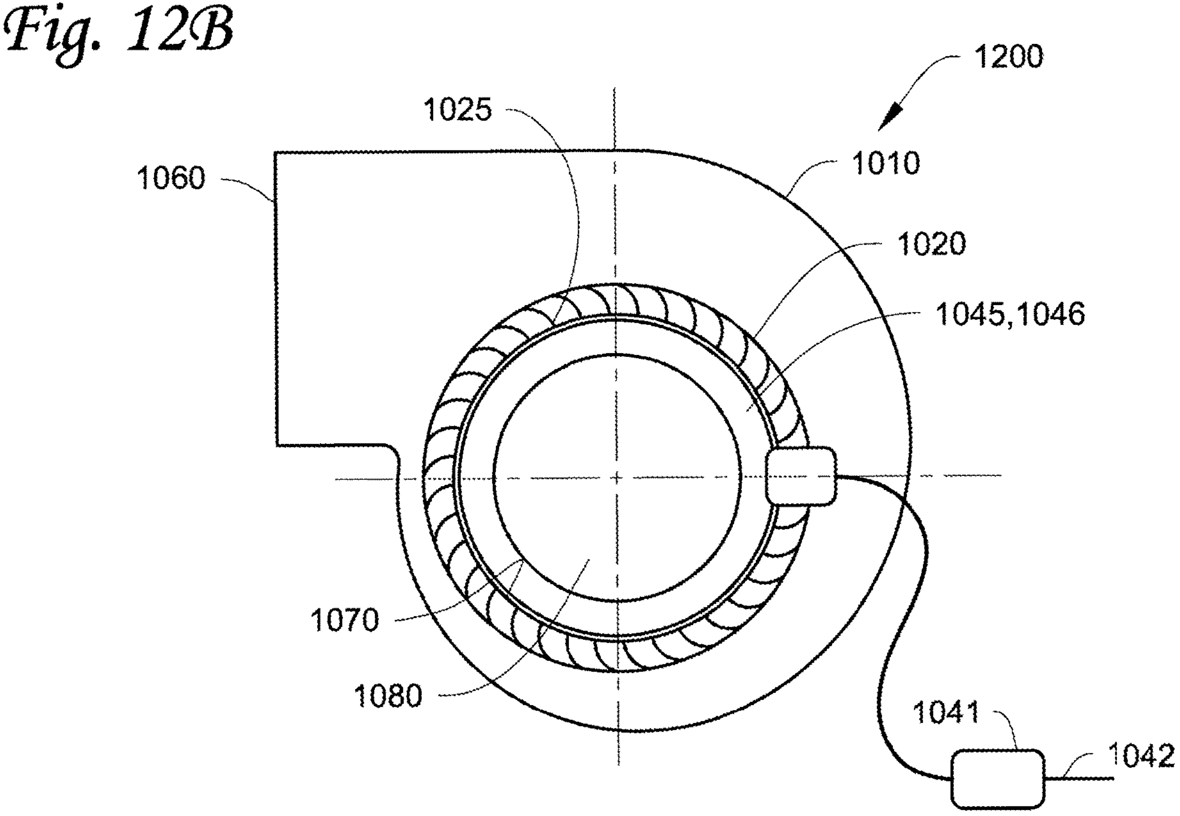

FIGS. 12A and 12B are perspective views of a centrifugal fan 1200 having light source(s), according to an embodiment. FIG. 12A is an end view of the centrifugal fan 1200 and FIG. 12B is a side view of the centrifugal fan 1200. In FIGS. 12A and 12B, each of the light source(s) 1045, 1046 can have a ring shape lamp that align with the shape of the curved inlet shroud 1070. In one embodiment, the light sources 1045, 1046 is/are disposed near or at end(s) 1011, 1012 of the centrifugal fan 1100 near or cover the curved inlet shroud 1070.

Embodiment disclosed herein can provide the light source(s) 1045, 1046 as e.g., rectifier ring(s) for air inlet rectification at the air inlet 1080. Such embodiments do not add resistance to the airflow due to the shape and location of the light source(s) 1045, 1046, and provide optimal aerodynamics. In such embodiments, due to the locations of the light source(s) 1045, 1046, some light from the light source(s) 1045, 1046 may not be emitted directly on the airflow nor on the photocatalyst layer on the inner surface of the volute housing 1010 and the outer surface of the impeller 1020 including outer surface of the plurality of fan blades 1025, and the power efficiency of the light may not be optimal.

Figure 13A:
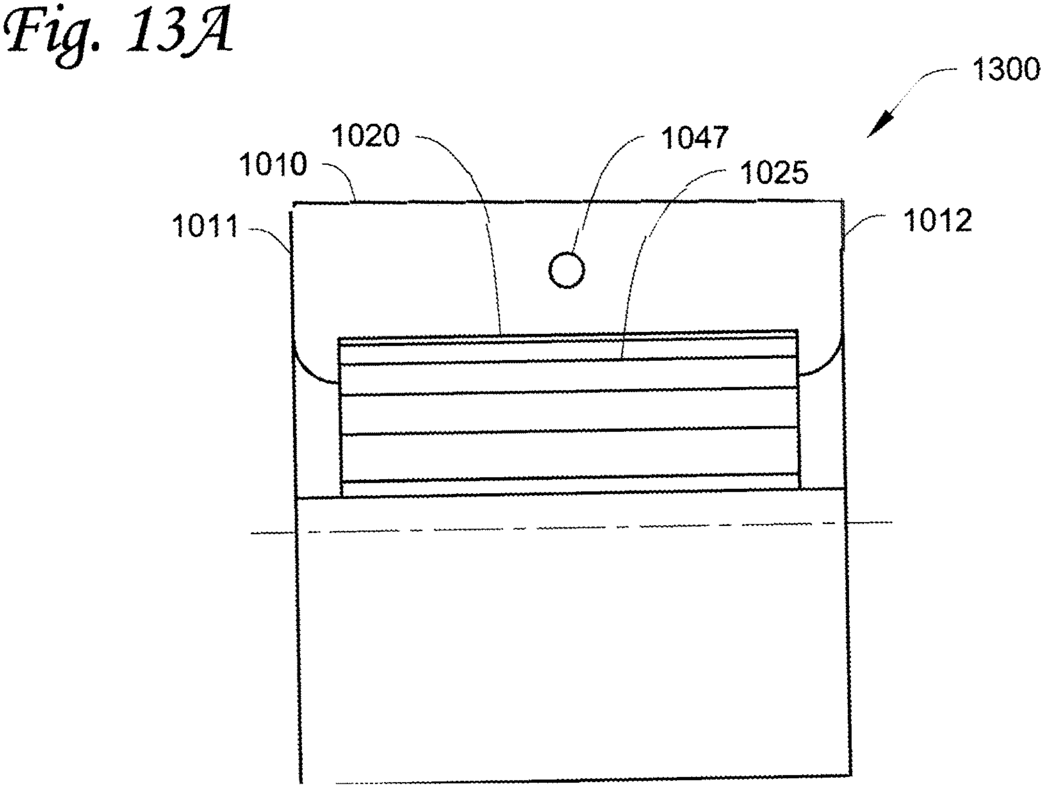
Figure 13B:
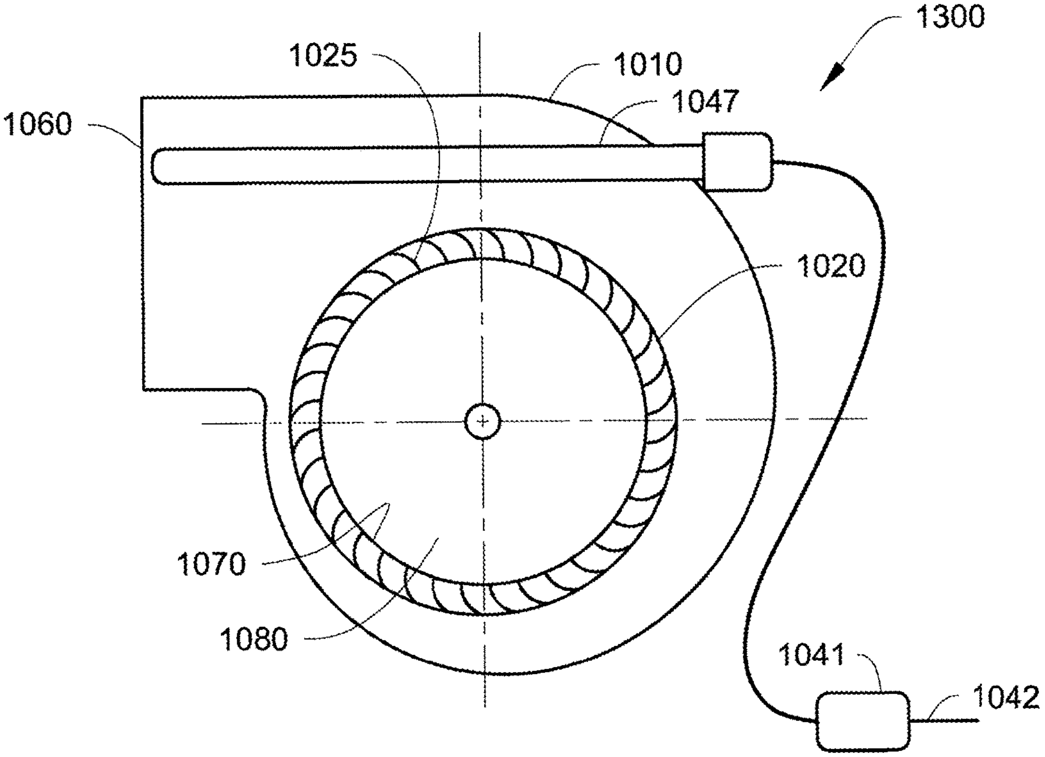

FIGS. 13A and 13B are perspective views of a centrifugal fan 1300 having light source(s), according to an embodiment. FIG. 13A is an end view of the centrifugal fan 1300 and FIG. 13B is a side view of the centrifugal fan 1300.

In FIGS. 13A and 13B, the light source 1047 is inserted (e.g., through a hole opened on the volute housing 1010) into the volute housing 1010 and extends toward the air outlet 1060 in a horizontal direction (substantially in parallel to an upper wall of the volute housing 1010). In one embodiment, the light source 1047 includes an elongated lamp extending near or at the air outlet 1060. The light source 1047 is disposed above the impeller 1020 and is closer to the upper wall (where the density of pathogens may be relatively high) of the volute housing 1010 than to the impeller 1020.

Embodiments disclosed herein provide a relatively closest distance of light (from the light source 1047) to the upper wall (where the density of pathogens is relatively high) of the volute housing 1010 to direct remove/kill pathogens (i.e., high efficiency of killing pathogens), and provide direct light from the light source 1047 onto most of the photocatalyst layer on the inner surface/walls of the volute housing 1010 and the outer surface of the impeller 1020 including outer surface of the plurality of fan blades 1025. It will be appreciated that such embodiments might not be optimal for aerodynamics, but provide a balanced solution regarding the efficiency of killing pathogens and the aerodynamics.

Figure 14A:
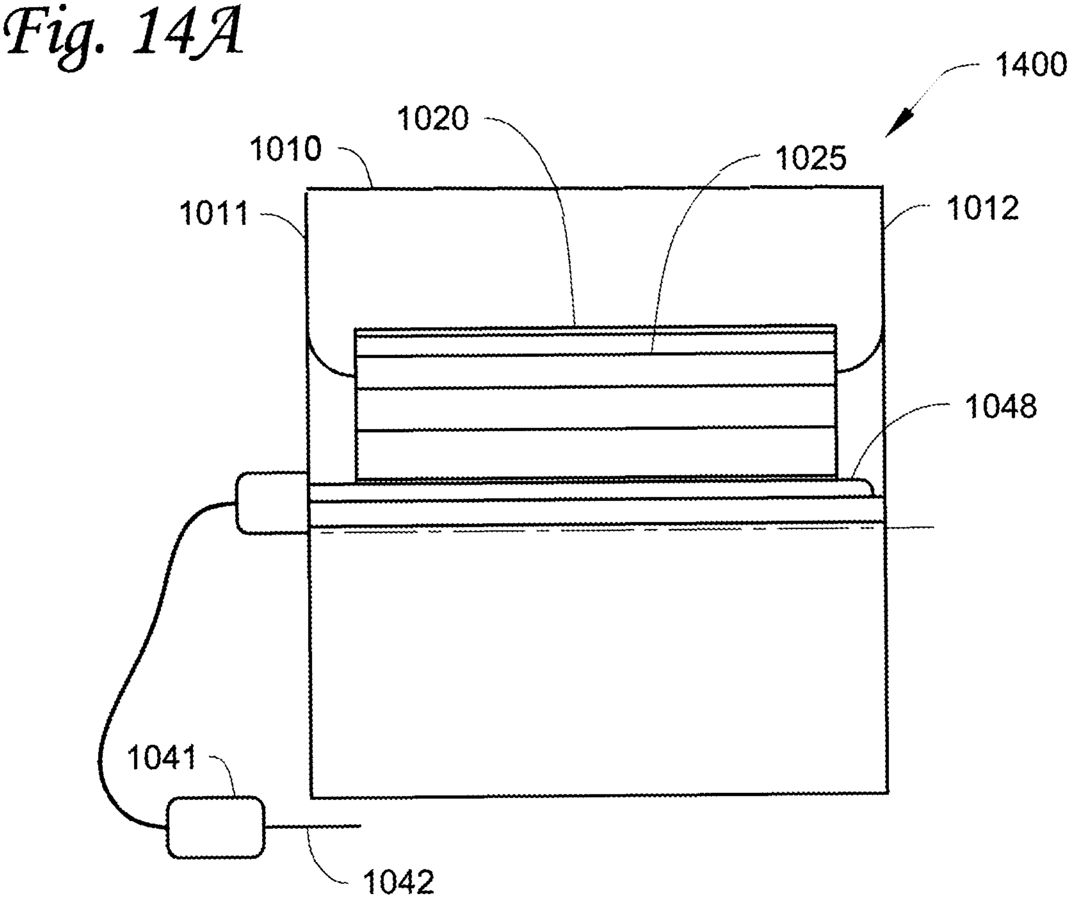
Figure 14B:
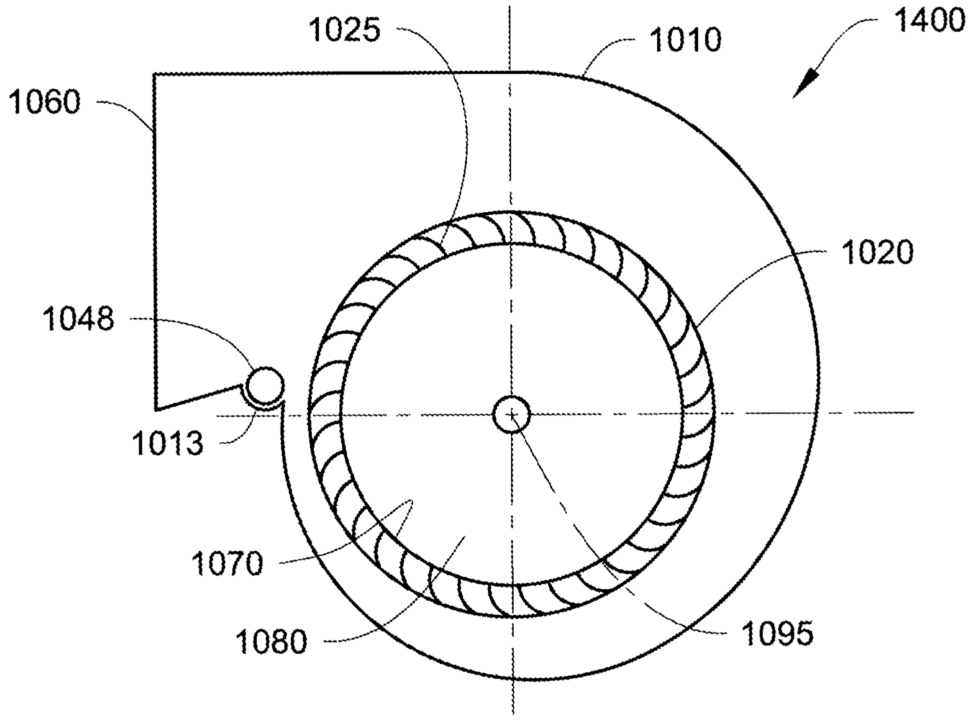

FIGS. 14A and 14B are perspective views of a centrifugal fan 1400 having light source(s), according to an embodiment. FIG. 14A is an end view of the centrifugal fan 1400 and FIG. 14B is a side view of the centrifugal fan 1400.

In FIGS. 14A and 14B, the volute housing 1010 includes a volute tongue 1013. The volute tongue 1013 is disposed close to the air outlet 1060. In one embodiment, the volute tongue 1013 has an arc shape for air rectification (to rectify the airflow), serves as a reflector made of polished aluminum or polished stainless steel or polytetrafluoroethylene to reflect the light emitted from the light source 1048 back into the volute housing 1010 (to e.g., prevent light leaking). In one embodiment, the volute tongue 1013 at least provides partial support to the light source 1048. The light source 1048 extends from a first side 1011 of the volute housing 1010 to a second side 1012 of the volute housing 1010. In one embodiment, a lower end of the air outlet 1060, the volute tongue 1013, and the rotational axis 1095 substantially aligned (e.g., horizontally) with each other. Embodiments disclosed herein can be optimal for aerodynamics.

Figure 15A:
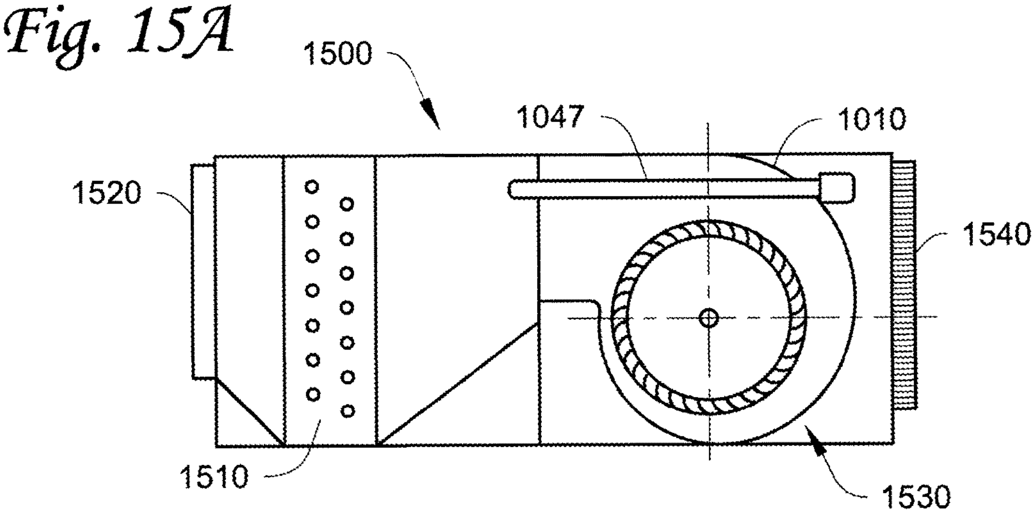

FIGS. 15A-15E are perspective views of a centrifugal fan having light source(s), according to an embodiment. FIG. 15A is a side view of an air handling unit 1500 including a centrifugal fan 1530. The unit 1500 includes an air outlet opening 1520 and a coil 1510. In one embodiment, the coil 1510 includes aluminum coil fin for outlet light (e.g., UV rays) blocking. It will be appreciated that the coil 1510 does not increase air-pressure drop. The unit 1500 also includes a screen 1540 disposed at or near the return air inlet of the unit 1500. In one embodiment, the screen 1540 is a honeycomb aluminum screen for inlet light (e.g., UV rays) blocking. It will be appreciated that the screen 1540 causes little or no air-pressure drop.

Figure 15B:
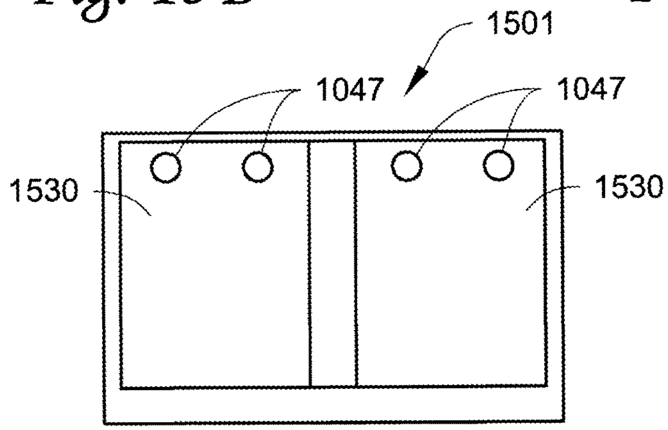
Figure 15C:
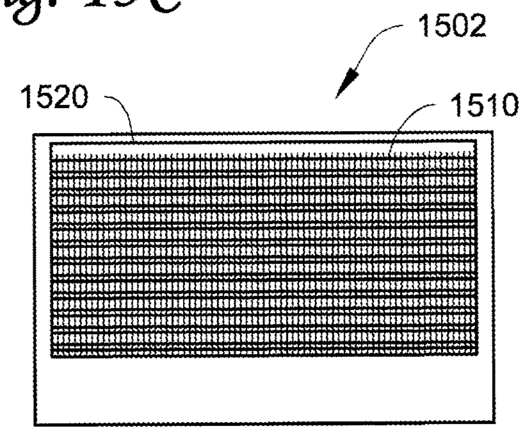
Figure 15D:
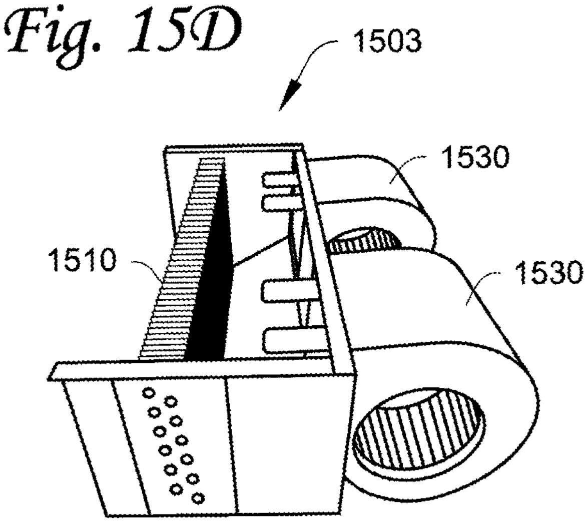
Figure 15E:
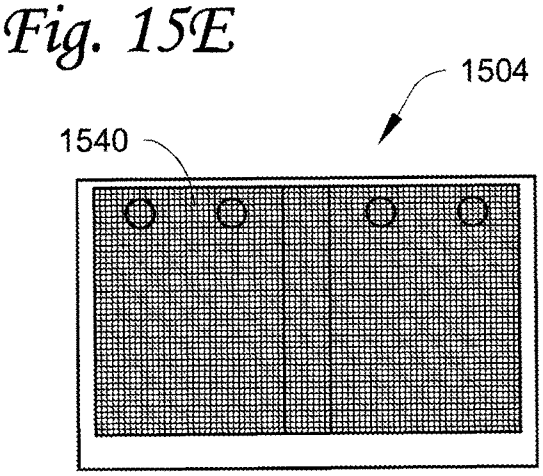

FIG. 15C is an end view 1502 of the unit 1500 facing the air outlet opening 1520, where the coil 1510 is visible. It is tested that in FIG. 15C, the UV intensity outside the air outlet opening 1520 is at or about 0.0 microwatts per centimeter$^2$. FIG. 15D is a top perspective view 1503 of the unit 1500 showing the coil 1510 and the centrifugal fan(s) 1530. FIG. 15E is an end view 1504 of the unit 1500 facing the screen 1540. It is tested that in FIG. 15E, the UV intensity outside the screen 1540 is at or about 0.0 microwatts per centimeter$^2$. FIG. 15B is an end view 1501 of the unit 1500 without the screen 1540. It is tested that in FIG. 15B, the UV intensity at the location (where the screen 1540 is in FIG. 15E) is at or about 56.1 microwatts per centimeter$^2$.

FIGS. 16A-16D are schematic views of a photocatalyst layer disposed on a surface (the surface is referred to as, e.g., inner surface of the volute housing and/or outer surface of the impeller including fan blades, or the volute housing and/or the fan blades) of a centrifugal fan, according to some embodiments.

Figure 16A:
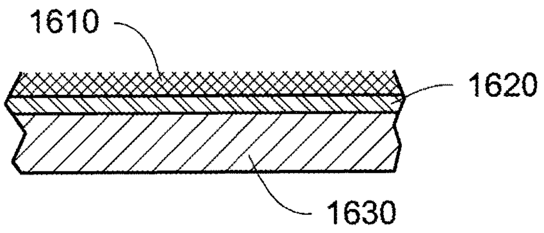
FIGS. 16A-16D are schematic views of a photocatalyst layer disposed on a surface of a centrifugal fan, according to some embodiments.
Figure 16B:
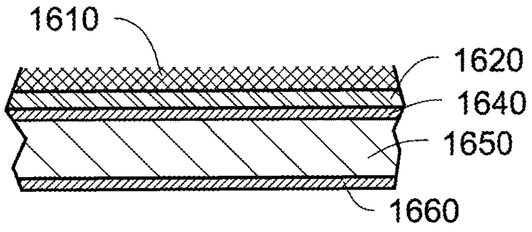

FIG. 16A shows that a primer layer 1620 is disposed on the surface of a centrifugal fan. The material of the primer can be polyurethane, passivation, etc. In one embodiment, the surface of the centrifugal fan is made of plastic 1630. The photocatalyst layer 1610 can be a titanium dioxide ($TiO_2$) layer disposed on top of the primer layer 1620. In FIG. 16B, the surface of the centrifugal fan is made of galvanized steel (1640 Zn, 1650 Steel, and 1660 Zn). It will be appreciated that the primer layer 1620 is configured to keep the photocatalyst layer 1610 on the surface (1630 or 1640-1660). The fan blades can be made of plastic or galvanized steel or the like.

In one embodiment, a primer layer can be added on the surface (1630 or 1640), and 10 nm (particle size) $TiO_2$ alcoholics can be added, along with 5 nm (particle size) $TiO_2$ aqua (e.g., $TiO_2$ powder adding water). It will be appreciated that the smaller the particle size of the $TiO_2$, the better efficacy for air filtering/disinfection.

Figure 16C:
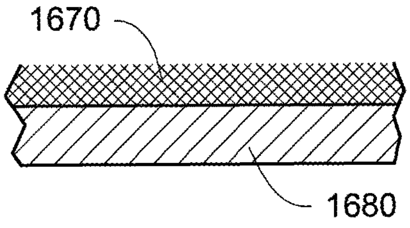
Figure 16D:
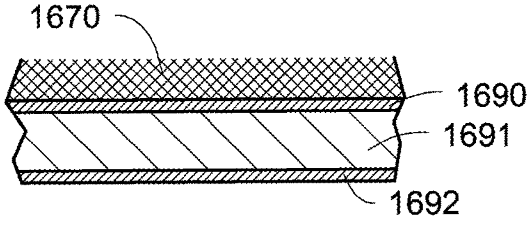

FIG. 16C shows that a photocatalyst layer 1670 is disposed on the surface of the centrifugal fan. In one embodiment, the surface is made of plastic 1680. The photocatalyst layer 1670 includes a titanium dioxide ($TiO_2$) layer having titanium dioxide on foamed polyurethane or foamed metal. In FIG. 16D, the surface of the centrifugal fan is made of galvanized steel (1690 Zn, 1691 Steel, and 1692 Zn). In one embodiment, a foamed $TiO_2$ layer (e.g., $TiO_2$ added on foamed nickel, or $TiO_2$ added on sponge of polyurethane) can be added on the surface (1680 or 1690-1692). It will be appreciated that the foamed $TiO_2$ layer (which is relatively thick) may be applied to the surface of the volute housing. For impeller or fan blades, since the foamed $TiO_2$ layer is relatively thick, aerodynamics may not be optimal.

It will be appreciated that the photocatalyst layer (1610-1620 or 1670) can be coated or sintered (or using other methods as disclosed in U.S. 2020/0016587 and CN110075706A, the entire disclosure of which are hereby incorporated by reference herein) on the surface (1630 or 1640-1660 or 1680 or 1690-1692). It will also be appreciated that sintering process can help to remove unwanted material from e.g., the $TiO_2$ layer (1620, 1670) so that the $TiO_2$ can be exposed to more air or can be exposed more directly to air.

It will be further appreciated that $TiO_2$ is of low cost and can work with UV lights (UVA, UVB, and UVC; which have relative short wavelength and high energy, can activate TiO2, and can generate hole-electron pair to create hydroxyl radicals). Also it will be appreciated that UVC can kill pathogens directly (without relying on the photocatalyst layer).

In one embodiment, the photocatalyst layer can include $TiO_2$ or ZnO or any other suitable material to work with UV light lamp(s). In another embodiment, the photocatalyst layer can include doped $TiO_2$ or graphitic carbon nitrides such as g-C3N4 or any other suitable materials to work with visible light from visible light lamp(s) (such as LED, to create hydroxyl radicals). The photocatalyst layer can include many semiconductor materials, CdS, $WO_3$, $SnO_2$, $Fe_2O_3$, $ZrO_2$, PbS, $SiO_2$, ZnS, $SrTiO_3$, etc., and/or graphene-based photocatalysts, etc.

It will be appreciated that for maximum disinfection effect, UVC (e.g., in an embodiment, with at or about 254 nm wavelength) light source is preferred, forming a combination of photocatalytic oxidation and ultraviolet germicidal irradiation. UV leakage may be controlled to a level under the national standard (e.g., at or about 5 microwatt /cm$^2$).

It will also be appreciated that UVA light source is safer for a human-being. For example, the exposure limit of UVA (e.g., having at or about 370 nm to at or about 380 nm wavelength) is at or about 10,000 times that of 254 nm UVC's. For example, an 8-hour UVA exposure limit is at or about 6.0 mJ/cm$^2$ with at or about 254 nm wavelength, at or about $3.2*10^5$ mJ/cm$^2$ with at or about 370 nm wavelength, or at or about $5.7*10^5$ mJ/cm$^2$ with at or about 385 nm wavelength. It will further be appreciated that doped $TiO_2$ or g-C3N4 working with visible light source can provide no safety risk to human.

Embodiments disclosed herein can utilize the extensive contact between the airflow and the impeller blades and the inner wall of the volute housing, to improve the efficiency of killing pathogens such as COVID-19.

Self-clean, regeneration, and super hydrophilicity tests have been conducted for the photocatalyst layer. The photocatalyst layer shows super hydrophilicity after e.g., UV light emitted on the photocatalyst layer. With water spay and the movement of the impeller, the photocatalyst layer can be easily cleaned of dirt or can self-clean the dirt on the photocatalyst layer, and the photocatalyst layer can be regenerated with water spray. Without replacing or changing the photocatalyst layer for a long period of time. In a self-cleaning test, $TiO_2$ shows photo-induced super hydrophilicity. For example, for 10 nm $TiO_2$ having contact angle at or about 60°, after UVC light irradiation for at or about 30 minutes, the contact angle is changed to at or about 16°. In a regeneration test, water spray can clean the photocatalyst layer and regenerate $TiO_2$ from deactivation.

ASPECTS

It is appreciated that any of aspects 1-19, 20, and 21-23 can be combined with each other.

Aspect 1. A centrifugal fan for a heating, ventilation, air conditioning, and refrigeration (HVACR) system, the centrifugal fan comprising:

a volute housing having an inner surface and a curved inlet shroud, the volute housing defining an air outlet, the curved inlet shroud defining an air inlet, and the air inlet having an inlet airflow cross-sectional area that lies substantially perpendicular to an outlet airflow cross-sectional area of the air outlet;

an impeller mounted for rotation about a rotational axis within the volute housing, the impeller having a plurality of fan blades, and the plurality of fan blades having an outer surface; and a light source, wherein the inner surface of the volute housing and the outer surface of the plurality of fan blades includes a photocatalyst layer, wherein the light source is configured to emit light on the photocatalyst layer.

Aspect 2. The centrifugal fan according to aspect 1, wherein the volute housing is made of plastic, the photocatalyst layer includes a primer layer disposed on the inner surface of the volute housing and the outer surface of the plurality of fan blades, and a titanium dioxide layer disposed on top of the primer layer.

Aspect 3. The centrifugal fan according to aspect 1, wherein the volute housing is made of galvanized steel, the photocatalyst layer includes a primer layer disposed on the inner surface of the volute housing and the outer surface of the plurality of fan blades, and a titanium dioxide layer disposed on top of the primer layer.

Aspect 4. The centrifugal fan according to aspect 1, wherein the volute housing is made of plastic, the photocatalyst layer includes a titanium dioxide layer having titanium dioxide on foamed polyurethane or foamed metal, the titanium dioxide layer is disposed on the inner surface of the volute housing and the outer surface of the plurality of fan blades.

Aspect 5. The centrifugal fan according to aspect 1, wherein the volute housing is made of galvanized steel, the photocatalyst layer includes a titanium dioxide layer having titanium dioxide on foamed polyurethane or foamed metal, the titanium dioxide layer is disposed on the inner surface of the volute housing and the outer surface of the plurality of fan blades.

Aspect 6. The centrifugal fan according to any one of aspects 1-5, wherein the photocatalyst layer is coated or sintered on the inner surface of the volute housing and the outer surface of the plurality of fan blades.

Aspect 7. The centrifugal fan according to any one of aspects 1-6, wherein the light source is configured to emit UVA light.

Aspect 8. The centrifugal fan according to any one of aspects 1-6, wherein the light source is configured to emit UVC light.

Aspect 9. The centrifugal fan according to any one of aspects 1-7, wherein the light source is a mercury lamp.

Aspect 10. The centrifugal fan according to any one of aspects 1-6, wherein the light source is a light-emitting diode light source.

Aspect 11. The centrifugal fan according to any one of aspects 1-10, wherein the volute housing includes a window that allows the light to pass through into an inner space of the volute housing, the centrifugal fan includes a reflector covering the window, the reflector is configured to reflect the light, and the light source is enclosed by the window and the reflector.

Aspect 12. The centrifugal fan according to aspect 11, wherein the window is made of silica glass, the reflector is made of polished aluminum or polished stainless steel or polytetrafluoroethylene, wherein the light source, the window, and the reflector extend from a first side of the volute housing to a second side of the volute housing.

Aspect 13. The centrifugal fan according to any one of aspects 1-10, wherein the light source is disposed inside a chamber of the centrifugal fan.

Aspect 14. The centrifugal fan according to aspect 13, wherein the light source includes a first light source and a second light source, the impeller includes a partition, the first light source extends from a first side of the volute housing toward the partition, and the second light source extends from a second side of the volute housing toward the partition.

Aspect 15. The centrifugal fan according to any one of aspects 1-10, wherein the light source has a ring-shape and is disposed at a side of the volute housing.

Aspect 16. The centrifugal fan according to any one of aspects 1-10, wherein the light source includes a first light source and a second light source, the first light source has a ring-shape and is disposed at a first side of the volute housing, the second light source has a ring-shape and is disposed at a second side of the volute housing.

Aspect 17. The centrifugal fan according to any one of aspects 1-10, wherein the light source is inserted in the volute housing in a direction toward the air outlet of the volute housing.

Aspect 18. The centrifugal fan according to any one of aspects 1-10, wherein the light source is disposed inside the volute housing near the air outlet, the light source extends from a first side of the volute housing to a second side of the volute housing.

Aspect 19. The centrifugal fan according to aspect 18, wherein the volute housing includes a reflector configured to reflect the light, the light source is disposed on the reflector.

Aspect 20. A method of configuring a centrifugal fan for a heating, ventilation, air conditioning, and refrigeration (HVACR) system, the centrifugal fan including a volute housing having an inner surface and a curved inlet shroud, the volute housing defining an air outlet, the curved inlet shroud defining an air inlet, and the air inlet having an inlet airflow cross-sectional area that lies substantially perpendicular to an outlet airflow cross-sectional area of the air outlet; an impeller mounted for rotation about a rotational axis within the volute housing, the impeller having a plurality of fan blades, and the plurality of fan blades having an outer surface; and a light source, the method comprising:

coating or sintering a photocatalyst layer on the inner surface of the volute housing and the outer surface of the plurality of fan blades, and emitting light, by the light source, on the photocatalyst layer.

Aspect 21. A heating, ventilation, air conditioning, and refrigeration (HVACR) system, the system comprising:

a compressor, a condenser, an expansion device, and an evaporator fluidly connected; and a centrifugal fan for the condenser or the evaporator, the centrifugal fan comprising:

a volute housing having an inner surface and a curved inlet shroud, the volute housing defining an air outlet, the curved inlet shroud defining an air inlet, and the air inlet having an inlet airflow cross-sectional area that lies substantially perpendicular to an outlet airflow cross-sectional area of the air outlet;

an impeller mounted for rotation about a rotational axis within the volute housing, the impeller having a plurality of fan blades, and the plurality of fan blades having an outer surface; and a light source, wherein the inner surface of the volute housing and the outer surface of the plurality of fan blades includes a photocatalyst layer, wherein the light source is configured to emit light on the photocatalyst layer.

Aspect 22. The HVACR system according to aspect 21, wherein the HVACR system is a climate control unit of a climate controlled transport unit.

Aspect 23. The HVACR system according to aspect 21, wherein the HVACR system is configured for a building space or an occupied space.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts without departing from the scope of the present disclosure. This specification and the embodiments described are exemplary only, with the true scope and spirit of the disclosure being indicated by the claims that follow.

What is claimed is:

1. A centrifugal fan for a heating, ventilation, air conditioning, and refrigeration (HVACR) system, the centrifugal fan comprising:

a volute housing having an inner surface and a curved inlet shroud, the volute housing defining an air outlet, the curved inlet shroud defining an air inlet, and the air inlet having an inlet airflow cross-sectional area that lies substantially perpendicular to an outlet airflow cross-sectional area of the air outlet;

an impeller mounted for rotation about a rotational axis within the volute housing, the impeller having a plurality of fan blades, and the plurality of fan blades having an outer surface; and a light source, wherein the inner surface of the volute housing and the outer surface of the plurality of fan blades includes a photocatalyst layer, wherein the light source is configured to emit light on the photocatalyst layer, wherein the volute housing includes a window that allows the light to pass through into an inner space of the volute housing, the window forms a part of the volute housing, the centrifugal fan includes a reflector covering the window, the reflector is configured to reflect the light, and the light source is enclosed by the window and the reflector.

2. The centrifugal fan according to claim 1, wherein the volute housing is made of plastic, the photocatalyst layer includes a primer layer disposed on the inner surface of the volute housing and the outer surface of the plurality of fan blades, and a titanium dioxide layer disposed on top of the primer layer.

3. The centrifugal fan according to claim 1, wherein the volute housing is made of galvanized steel, the photocatalyst layer includes a primer layer disposed on the inner surface of the volute housing and the outer surface of the plurality of fan blades, and a titanium dioxide layer disposed on top of the primer layer.

4. The centrifugal fan according to claim 1, wherein the volute housing is made of plastic, the photocatalyst layer includes a titanium dioxide layer having titanium dioxide on foamed polyurethane or foamed metal, the titanium dioxide layer is disposed on the inner surface of the volute housing and the outer surface of the plurality of fan blades.

5. The centrifugal fan according to claim 1, wherein the volute housing is made of galvanized steel, the photocatalyst layer includes a titanium dioxide layer having titanium dioxide on foamed polyurethane or foamed metal, the titanium dioxide layer is disposed on the inner surface of the volute housing and the outer surface of the plurality of fan blades.

6. The centrifugal fan according to claim 1, wherein the photocatalyst layer is coated or sintered on the inner surface of the volute housing and the outer surface of the plurality of fan blades.

7. The centrifugal fan according to claim 1, wherein the light source is configured to emit UVA light or UVC light.

8. The centrifugal fan according to claim 1, wherein the light source is a mercury lamp.

9. The centrifugal fan according to claim 1, wherein the light source is a light-emitting diode light source.

10. The centrifugal fan according to claim 1, wherein the window is made of silica glass, the reflector is made of polished aluminum or polished stainless steel or polytetrafluoroethylene, wherein the light source, the window, and the reflector extend from a first side of the volute housing to a second side of the volute housing.

11. The centrifugal fan according to claim 1, wherein the light source is disposed inside a chamber of the centrifugal fan.

12. The centrifugal fan according to claim 11, wherein the light source includes a first light source and a second light source, the impeller includes a partition, the first light source extends from a first side of the volute housing toward the partition, and the second light source extends from a second side of the volute housing toward the partition.

13. The centrifugal fan according to claim 1, wherein the light source has a ring-shape and is disposed at a side of the volute housing.

14. The centrifugal fan according to claim 1, wherein the light source includes a first light source and a second light source, the first light source has a ring-shape and is disposed at a first side of the volute housing, the second light source has a ring-shape and is disposed at a second side of the volute housing.

15. The centrifugal fan according to claim 1, wherein the light source extends in a direction toward the air outlet of the volute housing.

16. The centrifugal fan according to claim 1, wherein the light source is disposed closer to the air outlet than to the air inlet, the light source extends from a first side of the volute housing to a second side of the volute housing.

17. A method of configuring a centrifugal fan for a heating, ventilation, air conditioning, and refrigeration (HVACR) system, the centrifugal fan including a volute housing having an inner surface and a curved inlet shroud, the volute housing defining an air outlet, the curved inlet shroud defining an air inlet, and the air inlet having an inlet airflow cross-sectional area that lies substantially perpendicular to an outlet airflow cross-sectional area of the air outlet; an impeller mounted for rotation about a rotational axis within the volute housing, the impeller having a plurality of fan blades, and the plurality of fan blades having an outer surface; and a light source, the method comprising:

coating or sintering a photocatalyst layer on the inner surface of the volute housing and the outer surface of the plurality of fan blades, and emitting light, by the light source, on the photocatalyst layer, wherein the volute housing includes a window that allows the light to pass through into an inner space of the volute housing, the window forms a part of the volute housing, the centrifugal fan includes a reflector covering the window, the reflector is configured to reflect the light, and the light source is enclosed by the window and the reflector.

18. A heating, ventilation, air conditioning, and refrigeration (HVACR) system, the system comprising:

a compressor, a condenser, an expansion device, and an evaporator fluidly connected; and a centrifugal fan for the condenser or the evaporator, the centrifugal fan comprising:

a volute housing having an inner surface and a curved inlet shroud, the volute housing defining an air outlet, the curved inlet shroud defining an air inlet, and the air inlet having an inlet airflow cross-sectional area that lies substantially perpendicular to an outlet airflow cross-sectional area of the air outlet;

an impeller mounted for rotation about a rotational axis within the volute housing, the impeller having a plurality of fan blades, and the plurality of fan blades having an outer surface; and a light source, wherein the inner surface of the volute housing and the outer surface of the plurality of fan blades includes a photocatalyst layer, wherein the light source is configured to emit light on the photocatalyst layer, wherein the volute housing includes a window that allows the light to pass through into an inner space of the volute housing, the window forms a part of the volute housing, the centrifugal fan includes a reflector covering the window, the reflector is configured to reflect the light, and the light source is enclosed by the window and the reflector.

19. The HVACR system according to claim 18, wherein the HVACR system is a climate control unit of a climate controlled transport unit, or is configured for a building space or an occupied space.

* * * * *